US008877917B2

(12) United States Patent
Forst et al.

(10) Patent No.: US 8,877,917 B2
(45) Date of Patent: Nov. 4, 2014

(54) GLYCOCONJUGATES OF RNA INTERFERENCE AGENTS

(75) Inventors: Andrea Forst, Bayreuth (DE); Philipp Hadwiger, Kulmbach (DE); Hans-Peter Vornlocher, Bayreuth (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 1181 days.

(21) Appl. No.: 12/108,253

(22) Filed: Apr. 23, 2008

(65) Prior Publication Data
US 2009/0203135 A1 Aug. 13, 2009

Related U.S. Application Data

(60) Provisional application No. 60/925,880, filed on Apr. 23, 2007.

(51) Int. Cl.
| | | |
|---|---|---|
| C07H 21/04 | (2006.01) | |
| A61K 47/48 | (2006.01) | |
| C12N 15/113 | (2010.01) | |
| C12N 15/11 | (2006.01) | |

(52) U.S. Cl.
CPC ....... *A61K 47/48215* (2013.01); *C12N 2310/14* (2013.01); *C12N 2320/32* (2013.01); *C12N 2310/351* (2013.01); *C12N 15/113* (2013.01); *C12N 15/111* (2013.01); *A61K 47/48092* (2013.01)
USPC ....................................................... 536/24.5

(58) Field of Classification Search
USPC ....................................................... 536/24.5
See application file for complete search history.

(56) References Cited

U.S. PATENT DOCUMENTS

| | | | |
|---|---|---|---|
| 5,994,517 A | 11/1999 | Ts'o et al. | |
| 7,491,805 B2 | 2/2009 | Vargeese et al. | |
| 2003/0148928 A1 | 8/2003 | Beigelman et al. | |
| 2004/0259247 A1* | 12/2004 | Tuschl et al. | 435/375 |
| 2006/0148740 A1 | 7/2006 | Platenburg | |
| 2009/0325297 A1* | 12/2009 | Tian et al. | 435/455 |

FOREIGN PATENT DOCUMENTS

| | | | |
|---|---|---|---|
| EP | 0 957 107 A | 11/1999 | |
| WO | WO 99/52932 A | 10/1999 | |
| WO | 99 65925 A1 | 12/1999 | |
| WO | WO 02/085908 A | 10/2002 | |
| WO | WO 02/094185 | 11/2002 | |
| WO | 2004 024757 A2 | 3/2004 | |
| WO | WO 2004094595 A2 * | 11/2004 | |
| WO | WO 2006/020768 A | 2/2006 | |
| WO | WO 2006/078278 A | 7/2006 | |

OTHER PUBLICATIONS

Hamzavi R. et al.: "Modulation of the Pharmacokinetic Properties of PNA: Preparation of Galactosyl, Mannosyl, Fucosyl, N-Acetylgalactosaminyl, and N-Acetylglucosaminyl Derivatives of Aminoethylglycine Peptide Nucleic Acid Monomers and Their Incorporation into PNA Oligomers," Bioconjugate Chemistry, ACS, Washington, DC, US, vol. 14, Jan. 1, 2003, pp. 941-954, XP002270930; ISSN: 1043-1802.
Zheng, Sun-Jen et al.: "Distribution and anti-HBV effects of antisense oligodeoxynucleotides conjugated to galactosylated poly-L-lysine," World Journal of Gastroenterology, vol. 9, No. 6, 2003, pp. 1251-1255, XP002510287.
Mahato, R.I. et al.: "Physicochemical and Disposition Characteristics of Antisense Oligonucleotides Complexed with Glycosylated Poly(L-lysine)," Biochemical Pharmacology, Pergamon, Oxford, GB, vol. 53, Jan. 1, 1997, pp. 887-895, XP000197861, ISSN: 0006-2952.
Maier, M.A. et al.: "Synthesis of Antisense Oligonucleotides Conjugated to a Multivalent Carbohydrate Cluster for Cellular Targeting," Bioconjugate Chemistry, vol. 14, 2003, pp. 18-29, XP002510288.
Biessen, E.A., et al.: "The Cholesterol Derivative of a Triantennary Galactoside with High Affinity for Hepatic Asialoglycoprotein Receptor: A Potent Cholesterol Lowering Agent", Journal of Medicinal Chemistry, vol. 38(11), 1995, pp. 1846-1852.
Biessen, Erik A. L., et al.: "Synthesis of Cluster Galactosides with High Affinity for the Hepatic Asialoglycoprotein Receptor", Journal of Medicinal Chemistry, vol. 38(9), 1995, pp. 1538-1546.
Choi, Youngseon, et al.: "Targeting Cancer Cells with DNA-Assembled Dendrimers: A Mix and Match Strategy for Cancer", Cell Cycle, vol. 4(5), 2005, pp. 669-671.
Crossman, Arthur Jr., et al.: "Synthesis of Some Second-Generation Substrate Analogues of Early Intermediates in the Biosynthetic Pathway of Glycosylphosphatidylinositol Membrane Anchors", Carbohydrate Research, vol. 321(1-2), 1999, pp. 42-51.
Dubber, Michael, et al.: "Solid-Phase Synthesis of Multivalent Glycoconjugates on a DNA Synthesizer", Bioconjugate Chemistry, vol. 14(1), 2003, pp. 239-246.
Guo, S., et al.: "Construction of Folate-Conjugated pRNA of Bateriophase phi29 DNA Packaging Motor for Delivery of Chimeric siRNA to Nasopharyngeal Carcinoma Cells", Gene Therapy, vol. 13(10), 2006, pp. 814-820.
Ikeda, Yutaka, et al.: "Ligand-Targeted Delivery of Therapeutic siRNA", Pharmaceutical Research, vol. 23(8), 2006, pp. 1631-1640.
Karskela, Marika, et al.: "Synthesis and Cellular Uptake of Fluorescently Labeled Multivalent Hyaluronan Disaccharide Conjugates of Oligonucleotide Phosphorothioates", Bioconjugate Chemistry, vol. 19(12), 2008, pp. 2549-2558.
Katajisto, Johanna, et al.: "An Aminooxy-Functionalized Non-Nucleosidic Phosphoramidite for the Construction of Multiantennary Oligonucleotide Glycoconjugates on a Solid Support", Current Protocols in Nucleic Acid Chemistry, 2005, pp. 4.26.1-4.26.16.

(Continued)

*Primary Examiner* — J. E. Angell
(74) *Attorney, Agent, or Firm* — Jeffrey N. Townes; LeClairRyan

(57) ABSTRACT

The present invention relates to agents, compositions and methods for inhibiting the expression of a target gene, comprising an RNAi agent bearing at least one galactosyl moiety. These are useful for delivering the gene expression inhibiting activity to cells, particularly hepatocytes, and more particularly in therapeutic applications.

15 Claims, 7 Drawing Sheets

(56) References Cited

OTHER PUBLICATIONS

Katajisto, Johanna, et al.: "Solid-Phase Synthesis of Oligonucleotide Glycoconjugates Bearing Three Different Glycosyl Groups: Orthoganally Protected Bis (Hydroxymethy1)-N, N'-bis(3-Hydroxyproply)Malondiamide Phosphoramidite as Key Building Block", Journal of Organic Chemistry, vol. 69(22), 2004, pp. 7609-7615.

Katajisto, Johanna, et al.: "Solid-Phase Synthesis of Multiantennary Oligonucleotide Glycoconjugates Utilizing On-Support Oximation", Bioconjugate chemistry, vol. 15(4), 2004, pp. 890-896.

Li, Song, et al.: "Folate-Mediated Targeting of Antisense Oligodeoxynucleotides to Ovarian Cancer Cells", Pharmaceutical Research, vol. 15(10), 1998, pp. 1540-1545.

Liu, J., et al.: "Targeted Drug Delivery to Chemoresistant Cells: Folic Acid Derivatization of FdUMP [10] Enhances Cytotoxicity Toward 5-FU-Resistant Human Colorector Tumor Cells", Journal of Organic Chemistry, vol. 66(17), 2001, pp. 5655-5663.

Mahato, R. I., et al.: "Modulation of Gene Expression by Antisense and Antigene Oligodeoxynucleotides and Small Interfering RNA", Expert Opinion on Drug Delivery, 2005, vol. 2(1), pp. 3-28.

Murata, J. et al.: "Design of Quaternary Chitosan Conjugate Having Antennary Galactose Residues as a Gene Delivery Tool", Carbohydrate Polymers, vol. 32(2), 1997, pp. 105-109.

Rensen, Patrick, C. N., et al.: "Design and Synthesis of Novel N-Acetylgalactosamine-Terminated Glycolipids for Targeting of Lipoproteins to the Hepatic Asialoglycoprotein Receptor", Journal of Medicinal Chemistry, vol. 47(23), 2004, pp. 5798-5808.

Sioud, M.: "On the Delivery of Small Interfering RNAs into Mammalian Cells", Expert Opinion on Drug Delivery, vol. 2(4), 2005, pp. 639-651.

Six, L., et al.: "An Efficient and Stereoselective Synthesis of 1, 2-0-Dialkyl-3-0-Beta-D-Glycosyl-SN—Glycerols", Tetrahedron Letters, vol. 24(12), 1983, pp. 1229-1232.

Six, L., et al.: "Influence of Carbohydrate Moities on Monolayer Properties of Dialkylglyceryletherglycosides, Simple Model Compounds of the Glycolipids of Halophilic Bacteria", Journal of Colloid and Interface Science, vol. 93(1), 1983, pp. 109-114.

Sliedregt, Leo A. J. M., et al.: "Design and Synthesis of Novel Amphiphilic Dendritic Galactosides for Selective Targeting of Liposomes to the Hepatic Asialoglycoprotein Receptor", Journal of Medicinal Chemistry, vol. 42(4), 1999, pp. 609-618.

Vaino, A. R., et al.: "Synthesis of a D-Lactosyl Cluster-Nucleoside Conjugate", Chemical Communications, No. 19, 1997, pp. 1871-1872.

Wong, A., et al.: "Lipid, Sugar and Liposaccharide Based Delivery Systems", Current Medicinal Chemistry, vol. 8(9), 2001, pp. 1123-1136.

Zatsepin, Timofei S., et al.: "Synthesis and Applications of Oligonucleotide-Carbohydrate Conjugates", Chemistry & Biodiversity, vol. 1(10), 2004, pp. 1401-1417.

Zimmerman, T. S., et al.: "RNAi-Mediated Gene Silencing in Non-Human Primates", Nature, vol. 441(7089), 2006, pp. 111-114.

\* cited by examiner

SBGAL SBTEGGAL

SEQUENCE LISTING

```
<160> NUMBER OF SEQ ID NOS: 6

<210> SEQ ID NO 1
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (20)..(21)
<223> OTHER INFORMATION: Phosphorothioate linkage

<400> SEQUENCE: 1
gucaucacac ugaauaccaa u                                              21

<210> SEQ ID NO 2
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: 2'-O-methyl-modified c
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: modified_base
<222> LOCATION: (20)..(20)
<223> OTHER INFORMATION: 2'-O-methyl-modified a

<400> SEQUENCE: 2
auugguauua gugugugaca c                                              21

<210> SEQ ID NO 3
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
ggccuucuuu gaguucggug g                                              21
```

```
<210> SEQ ID NO 4
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: 2'-O-methyl-modified c
<220> FEATURE:
<221> NAME/KEY: modified_base
<222> LOCATION: (22)..(22)
<223> OTHER INFORMATION: 2'-O-methyl-modified a

<400> SEQUENCE: 4
ccaccgaacu caaagaaggc cac                                            23

<210> SEQ ID NO 5
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
ccacaugaag cagcacgacu u                                              21

<210> SEQ ID NO 6
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: 2'-O-methyl-modified g
<220> FEATURE:
<221> NAME/KEY: modified_base
<222> LOCATION: (22)..(22)
<223> OTHER INFORMATION: 2'-O-methyl-modified u

<400> SEQUENCE: 6
aagucgugcu gcuucaugug guc                                            23
```

GLYCOCONJUGATES OF RNA INTERFERENCE AGENTS

RELATED APPLICATIONS

This application claims the benefit of priority to U.S. Provisional Patent Application Ser. No. 60/925,880, filed Apr. 23, 2007; the entirety of which is hereby incorporated by reference.

FIELD OF THE INVENTION

The present invention relates to agents, compositions and methods for inhibiting the expression of a target gene, comprising an RNAi agent bearing at least one galactosyl-moiety. These are useful for delivering the gene expression inhibiting activity to cells, particularly hepatocytes, and more particularly in therapeutic applications.

BACKGROUND OF THE INVENTION

RNA interference (RNAi) is an evolutionarily conserved, sequence specific mechanism triggered by double stranded RNA (dsRNA) that induces degradation of complementary target single stranded mRNA and "silencing" of the corresponding translated sequences (McManus and Sharp, Nature Rev. Genet. 2002, 3:737; Mello and Donte, Nature 2004, 431:338; Meister and Tuschl, Nature 2004, 431:343; Sen and Blau, FASEB J. 2006, 20:1293).

Exploiting this mechanism has yielded a powerful tool to unravel the function and significance of hitherto unknown or uncharacterized genes in in vitro experiments (Hannon and Rossi, Nature 2004, 431:371; Westbrook et al., Cold Spring Harb Symp Quant Biol. 2005, 70:435): RNAi can be used to down-regulate or silence the transcription and translation of a gene product of interest; where said gene product is unknown or uncharacterized, the development of a certain phenotype can be used to determine the function and/or significance of the gene product. Great potential is also seen in harnessing the underlying cellular mechanisms for the therapy of human disease (Zhou et al., Curr Top Med. Chem. 2006, 6:901): where said gene product is in any way associated with a disease or disorder by way of its overabundance, its down-regulation may be used in the prevention and/or therapy of the disease or disorder.

The triggering of RNAi by dsRNA requires the dsRNA to be localized in the cytoplasm and/or nucleus of the cell in which the target gene is to be silenced. To this end, the dsRNA may be introduced directly into the cell, e.g., by bringing the cells into contact with the dsRNA, whereupon the dsRNA is actively or passively internalized. Therein, the dsRNA may be large, e.g., comprising 100, 200, 400 or more base pairs. A large dsRNA will be processed in mammals by an RNAse III-like enzyme commonly called Dicer to smaller fragments of 21 to 23 base pairs. Alternatively, the dsRNA may be small, e.g., of the size of the Dicer products (dsRNAs of this size, e.g., having not more than 30 base pairs, are in the art often referred to as short interfering RNAs, or siRNAs). The small dsRNAs, be they a product of Dicer activity or directly introduced, are subsequently unwound by, and one strand of the small dsRNA is incorporated into, a protein complex termed RISC(RNA induced silencing complex). RISC then proceeds to cleave mRNAs having a sequence complementary to the RNA strand that was incorporated into RISC (Meister and Tuschl, Nature 2004, 431:343).

In order to harness RNAi for any purpose in vitro and/or in vivo, a nucleic acid molecule must somehow be introduced into a cell, preferably into a cell that forms part of a living organism, such as a mammal or a human. If RNA interference is to live up to its potential, the process of introducing the nucleic acid molecule should disrupt the natural functions of the cell as little as possible, particularly where the cell is part of a living organism. This problem is shared by, for example, many procedures in genetic engineering, as well as gene therapy. Numerous solutions have been proposed, none of which is so far fully satisfactory.

The liver is one particularly attractive target for therapeutic intervention for a number of reasons: a) it plays a central role in many vital functions of the human body, b) it is the first pass organ for many substances absorbed from the gut and receives a large part of cardiac output, c) it is involved in many diseases and unwanted conditions with high prevalence in humans, e.g., Alagille syndrome, alcoholic liver disease, alpha-1-antitrypsin deficiency, Budd-Chiari syndrome, biliary atresia, Byler disease, dyslipidemias, Carol i-disease, Crigler-Najjar Syndrome, Dubin-Johnson Syndrome, fatty liver, galactosemia, Gilbert syndrome, glycogen storage disease 1, hemangioma, hemochromatosis, hepatitis of viral or autoimmune etiology, liver cancer, liver fibrosis and cirrhosis, porphyria cutanea tarda, erythrohepatic protoporphyria, Rotor syndrome, sclerosing cholangitis, or Wilson disease.

In the development of a treatment of hepatic diseases and conditions, it would be advantageous to have the capability to specifically target the cells of the liver with a therapeutic agent, e.g., an RNAi agent.

One approach documented in the literature has been conjugating the nucleic acid to a cholesterol moiety (Soutschek, J., et al., Nature 2004, 432:173-178), wherein the target gene was ApoB. However, the nucleic acid showed inhibition of ApoB not exclusively in the liver, but also in the gut of experimental animals. For an antisense oligodesoxynucleotide (ODN), adding a second cholesteryl moiety was effective in directing uptake of up to nearly 90% of a certain dose of the ODN to the liver (Bijsterbosch, M. K., et al., J. Pharmacol. Exp. Ther. 2002; 302:619).

Alternatively, a number of authors have proposed conjugating various molecular species, including ODN, to ligand moieties, e.g., via a variety of linkers, which bind the asialoglycoprotein receptor, to enhance hepatic uptake (Wu, G. Y., Wu, C. H., J. Biol. Chem. 1988, 263:14621; Biessen, E. A., et al., J. Med. Chem. 1995, 38:1538; Biessen, E. A. L., et al., Biochem. J. 1999, 340:783; Joziasse, D. H., et al., Eur. J. Biochem. 2000, 267:6501; Rump, E. T., et al., Biochem. Pharmacol. 2000; 59:1407; Biessen, E. A., Methods Enzymol. 2000, 314:324; Rensen, P. C. N., et al., J. Biol. Chem. 2001, 276:37577; Rossenberg, S. M. W., et al., J. Biol. Chem. 2002, 277:45803). The asialoglycoprotein receptor (ASGPR) is a transmembrane glycoprotein (42 kDa) which mediates binding, internalization and degradation of extracellular glycoproteins that have exposed terminal galactose residues. The receptor is expressed on the surface of hepatocytes, and only of hepatocytes, in a polar manner, i.e., it is present on the sinusoidal and lateral plasma membranes, but not on the bile canalicular membrane. The mammalian hepatic ASGPR mediates the endocytosis and degradation of serum proteins from which terminal sialic residues have been removed. The exclusive localization of the ASGPR to the liver, as well as its natural function in transporting comparatively large molecules into the hepatocyte, make it an attractive option for a mediator of liver cell targeting of therapeutic substances.

The available nucleic acid delivery systems are not yet satisfactory in terms of safety and/or efficiency for their utilization in in vitro experimental applications and/or human diagnosis and therapy, and require further optimization.

The technical problem underlying the present invention is the provision of improved methods and means for the delivery into cells of nucleic acid molecules, and preferably of RNAi agents, which are useful in vitro and in vivo, preferably for human therapy. This problem has been solved by the provision of the embodiments as characterized herein below and in the claims.

SUMMARY OF THE INVENTION

In one aspect, the invention provides an RNAi agent for inhibiting the expression of a target gene in a cell, wherein the RNAi agent consists of, or consists essentially of, at least two mutually complementary oligoribonucleotide strands of between 15 and 30 nucleotides in length, wherein at least one of the oligoribonucleotide strands is coupled to a ligand comprising at least one linker group and at least one galactose moiety, and wherein at least one oligoribonucleotide strand is complementary to at least parts of an mRNA corresponding to the target gene. In one embodiment, the ligand comprises at least two galactose moieties. In another embodiment, the linker is a branched linker. In the RNAi agents of the invention, the distance between the galactose moieties may be at least 4 Å, at least 10 Å, at least 15 Å, or at least 20 Å. Preferably, the RNAi agent is capable of inhibiting the expression of the target gene. Preferably, the cell harbors the asialoglycoprotein receptor on its surface. The cell may be a hepatocyte.

In another aspect of the invention, a pharmaceutical composition comprising (i) at least one RNAi agent of the claim 1, and (ii) a pharmaceutical oligonucleotide strand is provided.

In yet another aspect of the invention, a method for the manufacture of the RNAi agent of the invention is provided, comprising the steps of (i) synthesizing said at least two mutually complementary oligoribonucleotide strands of between 15 and 30 nucleotides in length, wherein at least one of the oligoribonucleotide strands is coupled to a ligand comprising a linker group and at least one galactose moiety, and (ii) effecting the hybridization of said at least two mutually complementary oligoribonucleotide strands. Preferably, such method further encompasses the step of formulating the RNAi agent with a pharmaceutical oligonucleotide strand.

In yet another aspect, a method to introduce an RNAi agent into a cell is provided, comprising the steps of: (1) contacting the cell with an RNAi agent of the invention.

In yet another aspect, a method to treat a subject is provided, comprising the step of: administering to the subject a pharmaceutical composition of the invention. Said subject is preferably in need of a treatment for a disease or condition related to unwanted expression of a target gene in the liver. Said subject may be a vertebrate, more preferably a mammal, yet more preferably a human.

In yet another aspect, a cell comprising an RNAi agent of the invention is provided. Said cell may be a hepatocyte.

DETAILED DESCRIPTION OF THE INVENTION

Figure 1:
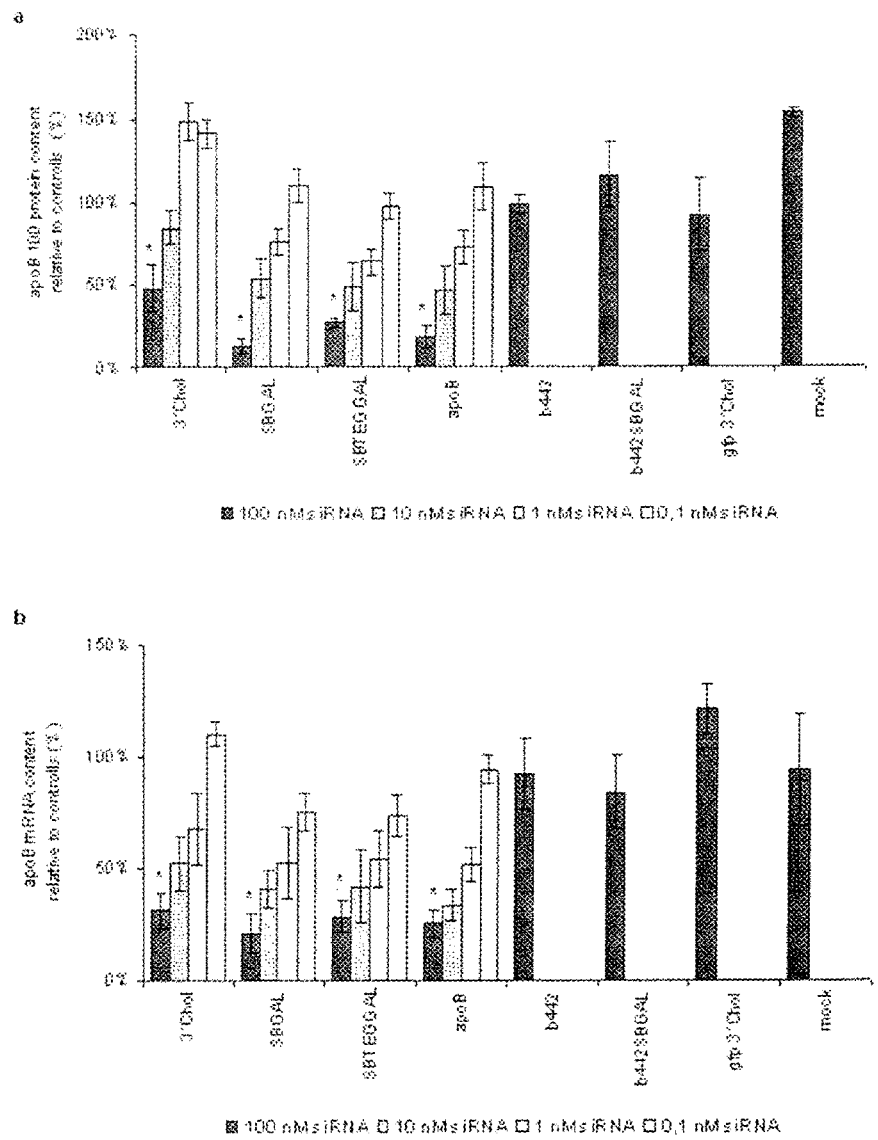
FIG. 1 depicts the effects of siRNA administration (100 nM, 10 nM, 1 nM and 0.1 nM) on apoB 100 protein and mRNA levels using oligofectamine in HuH7 cells. Protein content was measured by ELISA and mRNA content was determined by b-DNA. Data are presented as mean values with corresponding standard diviation of three assays in triplicates normalized to the average level of unspecific siRNAs. Statistical analysis was done by t-test, P*<0.001 compared to unspecific controls.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^3$ carbons may optionally serve as the point of attachment of the alkenyl and alkynyl groups, respectively.

The term "alkoxy" refers to an —O-alkyl radical. The term "aminoalkyl" refers to an alkyl substituted with an amino the term "mercapto" refers to an —SH radical. The term "thioalkoxy" refers to an —S-alkyl radical.

The term "alkylene" refers to a divalent alkyl (i.e., —R—), e.g., —$CH_2$—, —$CH_2CH_2$—, and —$CH_2CH_2CH_2$—. The term "alkylenedioxo" refers to a divalent species of the structure —O—R—O—, in which R represents an alkylene.

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

The term "cycloalkyl" as employed herein includes saturated cyclic, bicyclic, tricyclic, or polycyclic hydrocarbon groups having 3 to 12 carbons, wherein any ring atom can be substituted. The cycloalkyl groups herein described may also contain fused rings. Fused rings are rings that share a common bond. Examples of cycloalkyl moieties include, but are not limited to, cyclohexyl, adamantyl, norbornyl, and decalin.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom capable of substitution can be substituted by a substituent. The heterocyclyl groups herein described may also contain fused rings. Fused rings are rings that share a common bond. Examples of heterocyclyl include, but are not limited to tetrahydrofuranyl, tetrahydropyranyl, piperidinyl, morpholino, pyrrolinyl and pyrrolidinyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O or S if monocyclic, bicyclic, or tricyclic, respectively), wherein any ring atom can be substituted.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

An "RNAi agent", as used herein, means a molecule (a "molecule", as used herein, is the smallest unit of a substance that has all the properties of that substance; "molecule", therefore, does not necessarily imply, nor exclude, that all the atoms from which it is formed are linked by covalent bonds) consisting of, consisting essentially of, or comprising, at least two mutually complementary oligoribonucleotide strands of between 15 and 30 nucleotides in length, wherein at least one of the oligoribonucleotide strands is coupled to a ligand comprising at least one linker group and at least one galactose moiety, and wherein at least one oligoribonucleotide strand is complementary to at least parts of an mRNA corresponding to the target gene. The strand that is complementary to the target gene mRNA is herein referred to as the "antisense strand", the respective other strand as the "sense strand". By virtue of their mutual complementarity, the two strands are capable of hybridization, forming a duplex structure with between 15 and 30, and preferably 15, 16, 17, 18, 19, 20, 21, 22, 23, 24, 25, 26, 27, 28, 29 or 30 nucleotide pairs. The RNA strands may have the same or a different number of nucleotides, and each strand may individually and independently be 15, 16, 17, 18, 19, 20, 21, 22, 23, 24, 25, 26, 27, 28, 29 or 30 nucleotides in length. Ranges between any two of these numbers are also contemplated, both for the number of base pairs as well as for the length of the individual strands. The maximum number of base pairs is the number of nucleotides in the shortest strand.

The two strands may be complementary such that all of the nucleotides in both strands are involved in nucleotide pairs, or they may form single-stranded regions, such as one or more of overhangs, bulges, loops, etc. Overhangs, if present, are preferably of a length of 1-4, and more preferably 2 or 3 nucleotides in length. In one embodiment, the length of the overhang(s) does not exceed 100, or 50, or 20, or 10, or 5 nucleotides. They may be located at the 3'- or the 5'-end of either strand, but preferred embodiments comprise at least one overhang on the 3'-ends of the antisense strand, or of both strands.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop". Where the two strands are connected covalently by means other than an uninterrupted chain of nucleotides between the 3'-end of one strand and the 5'-end of the respective other strand forming the duplex structure, the connecting structure is referred to as a "strand linkage". Where the two strands are connected by a hairpin loop, and the duplex structure consists of not more than 30 nucleotide pairs, the RNAi agent may be referred to herein as a short hairpin RNA (shRNA). Where the two strands are not connected, or connected by a strand linkage, and the duplex structure consists of not more than 30 nucleotide pairs, the RNAi agent may be referred to herein as a short interfering RNA (siRNA).

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. "Complementary" sequences may be fully complementary, or they may include mismatches, as long as they are still able to hybridize under the chosen conditions. For purposes of the present invention, an overhang shall not be considered a mismatch. Preferably, complementary sequences will include not more than 1, not more than 2, not more than 3, not more than 4, or not more than 5 mismatches, if any. The degree of complementarity will, at any rate, be such that stable and specific binding occurs between the two oligonucleotides comprising the sequences referred to as complementary. Specific binding requires a sufficient lack of complementarity to non-target sequences under conditions in which specific binding is desired, i.e., under physiological conditions in the case of in vivo assays or therapeutic treatment, or in the case of in vitro assays, under conditions in which the assays are performed. It has been shown that a single mismatch between targeted and non-targeted sequences can be sufficient to provide discrimination for siRNA targeting of an mRNA (Brummelkamp et al., *Cancer Cell,* 2002, 2:243).

In one embodiment, an RNAi agent's antisense strand is "sufficiently complementary" to a target RNA, such that the RNAi agent inhibits production of protein encoded by the target mRNA. The target RNA can be, e.g., a pre-mRNA or mRNA endogenous to a subject or organism. In another embodiment, the RNAi agent is "fully complementary" to a target RNA, e.g., the target RNA and the RNAi agent can anneal to form a hybrid made exclusively of Watson-Crick base pairs in the region of exact complementarity. A "sufficiently complementary" RNAi agent antisense strand can include a region (e.g., of at least 7 nucleotides) that is exactly complementary to the target RNA. Moreover, in some embodiments, the RNAi agent specifically discriminates a single-nucleotide difference. In this case, the RNAi agent only down-regulates gene expression from an mRNA if exact complementarity is found in the region of the single-nucleotide difference.

"RNA", "oligoribonucleotide" and "oligoribonucleotide strand", as used herein, shall refer to nucleic acids having predominantly RNA-like properties, e.g., having the ability to hybridize to a substantially complementary RNA, forming an A-type helix. Generally, an RNA, oligoribonucleotide or oligoribonucleotide strand will consist mostly, or exclusively, of ribonucleotides, i.e., cytidine, adenosine, guanosine and uridine nucleosides interconnected by 5'-3'-monophosphate bridging groups. However, one or more, or all, nucleotides may be 2'-O-methyl ribonucleotides, or nucleotides not naturally occurring in RNA, for example, without limitation, deoxyribonucleotides, inosines, 2'-deoxy-2'-fluoro-, or 2'-O [(CH$_2$)$_n$O]$_m$CH$_3$ ribonucleotides, as long as the overall molecule retains predominantly RNA-like properties. In addition, or alternatively, the RNA may comprise modified internucleoside linkages, e.g., phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. Further nucleotide modifications are well known to the skilled person and are encompassed by the present invention, e.g., those described in WO 03/070918 and U.S. Pat. Nos. 3,687,808; 4,469,863; 4,476,301; 4,845,205; 4,981,957; 5,023,243; 5,034,506; 5,118,800; 5,134,066; 5,166,315; 5,175,273; 5,177,195; 5,185,444; 5,188,897; 5,214,134; 5,216,141; 5,235,033; 5,264,423; 5,264,564; 5,276,019; 5,278,302; 5,286,717; 5,319,080; 5,321,131; 5,359,044; 5,367,066; 5,393,878; 5,399,676; 5,405,938; 5,405,939; 5,432,272; 5,434,257; 5,446,137; 5,453,496; 5,455,233; 5,457,187; 5,459,255; 5,466,677; 5,466,677; 5,466,786; 5,470,967; 5,476,925; 5,484,908; 5,489,677; 5,502,177; 5,514,785; 5,519,126; 5,519,134; 5,525,711; 5,536,821; 5,541,307; 5,541,316; 5,550,111; 5,552,540; 5,561,225; 5,563,253; 5,567,811; 5,571,799; 5,576,427; 5,587,361; 5,587,469; 5,591,722; 5,594,121; 5,596,086; 5,596,091; 5,597,909; 5,602,240; 5,608,046; 5,610,289; 5,610,300; 5,614,617; 5,618,704; 5,623,070; 5,625,050; 5,627,053; 5,633,360; 5,639,873; 5,646,265; 5,658,873; 5,663,312; 5,670,633; 5,677,437; 5,677,439; 5,681,941; 5,700,920; 5,750,692, all of which are hereby incorporated herein by reference. Further embodiments are described below.

The introduction or transfer process of nucleic acid molecules of interest into a cell is by itself well known. "Introduction or transfer" means that the nucleic acid is, at the outset of the transfer process, located outside the cell or on the outer surface of the cell's membrane, and, at the end of the process, located inside said cell, or within its membrane, or on the inner surface of the membrane. The "introduction or transfer" of a nucleic acid molecule into a cell is also referred to as "transfection". Transfection can be verified by any appropriate method, for example by measuring a biological, chemical or physical effect associated with its presence inside the cell. In the case of RNAi agents, the effect to be measured may, for example, be the inhibition of the expression of the target gene of the RNAi agent.

At least one strand of the RNAi agents of the invention is coupled to a ligand comprising at least one linker group and at least one galactose moiety. "Coupled to a ligand", as used herein, means that the ligand is associated with the RNA strand in a manner that substantially prevents the separation of the ligand from the RNA strand under the conditions most relevant to the use of the RNAi agent, e.g., in blood or serum at 37° C. for therapeutics, or in cell growth media for RNAi agents for in vitro use. "Substantially prevents the separation of the ligand from the RNA strand" means that in the majority of the RNAi agent molecules, e.g., in more than 80%, more than 90%, more than 95%, more than 99%, or preferably more than 99.9% of RNAi agent molecules, the ligand remains associated with the RNA strand under the said conditions. Preferably, but not necessarily, the ligand is coupled to the RNA strand by means of a covalent bond. Alternatively, the coupling of the ligand to the RNA strand may be effected by, for example, van der Waals forces, hydrogen bonds, ionic interactions, or any other molecular interaction strong enough under the said conditions to substantially prevent the separation of the ligand from the RNA strand under the said conditions.

The ligand can be placed at an end of the RNA strand, preferably at the 3'-end. The ligand can also be placed at the 5' end, or within the middle of the RNA strand. In some embodiments, more than one ligand can be coupled to the RNA strand, or to both strands of the RNAi agent. For example, a ligand can be coupled to the 3' end of one RNA strand, e.g., the sense or antisense strand; a ligand can be coupled to an end, e.g., a 3' end, and to the middle of an RNA strand, e.g., the sense or antisense strand; a ligand can be coupled to the 3' end and the 5' of an RNA strand, e.g., the sense or antisense strand; a ligand can be coupled to the 3' end, the 5' end, and to one or more internal positions of an RNA strand, e.g., the sense or antisense strand; a ligand can be coupled to the 3'-end of both the sense and the antisense strands; a ligand can be coupled to the 5'-end of both the sense and the antisense strands; a ligand can be coupled to the 3'-end of the sense and the 5'-end of the sense strand, or vice versa; a ligand can be coupled to the 3'-end of both the sense and the antisense strands, and to an internal position on either strand, e.g., the sense and the antisense strand; the skilled person will readily envision further permutations of this scheme, which are all envisaged by the present invention.

The Galactose Moiety

The galactose moiety is a galactopyranosyl or, preferably, a N-acetyl galactosaminpyranosyl group of general formula $C_6(OR^1)(OR^2)(OR^3)(OR^4)(OR^6)O$ or $C_6(OR^1)(NHCH_2COOH)(OR^3)(OR^4)(OR^6)O$, wherein $(OR^1)$ is attached to the C1 position of the galactopyranose ring, $(OR^2)$ or $(NHCH_2COOH)$ is attached to the C2 position of the galactopyranose ring, $(OR^3)$ is attached to the C3 position of the galactopyranose ring, and so forth, and wherein each of $(OR^1)$—$(OR^4)$ and $(OR^6)$ are independently OH, lower alkyloxy or acyloxy ($C_1$-$C_6$), or replaced by one of the linker groups described below, but wherein at least one of $(OR^1)$—$(OR^4)$ and $(OR^6)$ is replaced by one of the linker groups described below. Preferably, $R^2$ (where present), $R^3$, $R^4$, and $R^6$ are H, and $(OR^1)$ is replaced by one of the linker groups described below. Preferably, the pyranose ring is in the β-anomeric conformation.

The presence of more than one, e.g., 2, 3, or 4 or more, galactose moieties markedly increases the affinity of a ligand for the asialoglycoprotein receptor, leading to increased transfection efficiency of the RNAi agent comprising such more than one galactose moities.

Linker Groups

The conjugation or coupling of the ligand to the RNA strand is mediated by the linker group, where only one linker group is present, or by one or more of the linker groups, if more than one linker group is present. The intended nature of the conjugation or coupling interaction will determine the choice of linker group.

In certain embodiments, a galactose moiety is coupled to an oligonucleotide strand via the intermediacy of an intervening linker group. Linker groups are connected to the oligonucleotide strand at a linker group attachment point (LAP) and may include any $C_1$-$C_{100}$ carbon-containing moiety, (e.g., $C_1$-$C_{75}$, $C_1$-$C_{50}$, $C_1$-$C_{20}$, $C_1$-$C_{10}$; $C_1$, $C_2$, $C_3$, $C_4$, $C_5$, $C_6$, $C_7$, $C_8$, Cg, or $C_{10}$), preferably having at least one oxygen atom, at least one phosphorous atom, and/or at least one nitrogen atom. In preferred embodiments, the phosphorous atom forms part of a terminal phosphate, or phosphorothioate, group on the linker group, which may serve as a connection point for the oligonucleotide strand. In preferred embodiments, the nitrogen atom forms part of a terminal ether, ester, amino or amido (NHC(O)—) group on the linker group, which may serve as a connection point for the galactose moiety. Preferred linker groups (underlined) include LAP-X—$(CH_2)_n$NH—; LAP-X—C(O)$(CH_2)_n$NH—; LAP-X—NR''''$(CH_2)_n$NH—, LAP-X—C(O)—$(CH_2)_n$—C(O)—; LAP-X—C(O)—$(CH_2)_n$—C(O)O—; LAP-X—C(O)—O—; LAP-X—C(O)—$(CH_2)_n$—NH—C(O)—; LAP-X—C(O)—$(CH_2)_n$; LAP-X—C(O)—NH—; LAP-X—C(O)—; LAP-X—$(CH_2)_n$—C(O)—; LAP-X—$(CH_2)_n$—C(O)O—; LAP-X—$(CH_2)_n$—; or LAP-X—$(CH_2)_n$—NH—C(O)—; in which —X is (—O—(R''''O)P(O)—O—)$_m$, (—O—(R''''O)P(S)—O—)$_m$, (—O—(R''''S)P(O)—O—)$_m$, (—O—(R''''S)P(S)—O—)$_m$, (—O—(R''''O)P(O)—S—)$_m$, (—S—(R''''O)P(O)—O—)$_m$, or nothing, n is 1-20 (e.g., 1, 2, 3, 4, 5, 6, 7, 8, 9, 10, 11, 12, 13, 14, 15, 16, 17, 18, 19, or 20), m is 1 to 3, and R'''' is H or $C_1$-$C_6$ alkyl. Preferably, n is 5, 6, or 11. In other embodiments, the nitrogen may form part of a terminal oxyamino group, e.g., —ONH$_2$, or hydrazino group, —NHNH$_2$. The linker group may optionally be substituted, e.g., with hydroxy, alkoxy, perhaloalkyl, and/or optionally inserted with one or more additional heteroatoms, e.g., N, O, or S. Preferred linker groups may include, e.g., LAP-X—$(CH_2)_n$NH—; LAP-X—C(O)$(CH_2)_n$NH—; LAP-X—NR''''$(CH_2)_n$NH—; LAP-X—$(CH_2)_n$ONH—; LAP-X—C(O)$(CH_2)_n$ONH—; LAP-X—NR''''$(CH_2)_n$ONH—; LAP-X—$(CH_2)_n$NHNH$_2$—, LAP-X—C(O)$(CH_2)_n$NHNH$_2$—; LAP-X—NR''''$(CH_2)_n$NHNH$_2$—; LAP-X—C(O)—$(CH_2)_n$—C(O)—; LAP-X—C(O)—$(CH_2)_n$—C(O)O—: LAP-X—C(O)—O—; LAP-X—C(O)—$(CH_2)_n$—NH—C(O)—; LAP-X—C(O)—$(CH_2)_n$—; LAP-X—C(O)—NH—; LAP-X—C(O)—; LAP-X—$(CH_2)_n$—C(O)—; LAP-X—$(CH_2)_n$—C(O)O—; LAP-X—$(CH_2)_n$—; or LAP-X—$(CH_2)_n$—NH—C(O)—. In some embodiments, amino terminated linker groups (e.g., NH$_2$, ONH$_2$, NH$_2$NH$_2$) can form an imino bond (i.e., C═N) with the ligand. In some embodiments, amino terminated linker groups (e.g., NH$_2$, ONH$_2$, NH$_2$NH$_2$) can be acylated, e.g., with C(O)CF$_3$.

In some embodiments, the linker group can terminate with a mercapto group (i.e., SH) or an olefin (e.g., CH═CH$_2$). For example, the linker group can be LAP-X—$(CH_2)_n$—SH, LAP-X—C(O)$(CH_2)_n$SH, LAP-X—$(CH_2)_n$—(CH═CH$_2$), or LAP-X—C(O)$(CH_2)_n$(CH═CH$_2$), in which X and n can be as described for the linker groups above. In certain embodiments, the olefin can be a Diels-Alder diene or dienophile. The linker group may optionally be substituted, e.g., with hydroxy, alkoxy, perhaloalkyl, and/or optionally inserted with one or more additional heteroatoms, e.g., N, O, or S. The double bond can be cis or trans or E or Z.

In other embodiments the linker group may include an electrophilic moiety, preferably at the terminal position of the linker group. Preferred electrophilic moieties include, e.g., an aldehyde, alkyl halide, mesylate, tosylate, nosylate, or brosylate, or an activated carboxylic acid ester, e.g., an NHS ester, or a pentafluorophenyl ester. Preferred linker groups (underlined) include LAP-X—$(CH_2)_n$CHO; LAP-X—C(O)$(CH_2)_n$CHO; or LAP-X—NR''''$(CH_2)_n$CHO, in which n is 1-6 and R'''' is $C_1$-$C_6$ alkyl; or LAP-X—$(CH_2)_n$C(O)ONHS; LAP-X—C(O)$(CH_2)_n$C(O)ONHS; or LAP-X—NR''''$(CH_2)_n$C(O)ONHS, in which n is 1-6 and R'''' is $C_1$-$C_6$ alkyl; LAP-X—$(CH_2)_n$C(O)OC$_6$F$_5$; LAP-X—C(O)$(CH_2)_n$C(O)OC$_6$F$_5$; or LAP-X—NR''''$(CH_2)_n$C(O)OC$_6$F$_5$ in which n is 1-11 and R'''' is $C_1$-$C_6$ alkyl; or —$(CH_2)_n$CH$_2$LG; LAP-X—C(O)$(CH_2)_n$CH$_2$LG; or LAP-X—NR''''$(CH_2)_n$CH$_2$LG, in which X, R'''' and n can be as described for the linker groups above (LG can be a leaving group, e.g., halide, mesylate, tosylate, nosylate, brosylate). Coupling the oligonucleotide-linker group to the galactose moiety can be carried out by coupling a nucleophilic group of the galactose moiety with an electrophilic group on the linker group.

In other embodiments, other protected amino groups can be at the terminal position of the linker group, e.g., alloc, monomethoxy trityl (MMT), trifluoroacetyl, Fmoc, or aryl sulfonyl (e.g., the aryl portion can be ortho-nitrophenyl or ortho, para-dinitrophenyl).

In any of the above linker groups, in addition, one, more than one, or all, of the n —CH$_2$— groups may be replaced by one or a combination of, e.g., X, as defined above, —Y—(CH$_2$)$_m$—, —Y—(C(CH$_3$)H)$_m$—, —Y—C((CH$_2$)$_p$CH$_3$)H)$_m$—, —Y—(CH$_2$—C(CH$_3$)H)$_m$—, —Y—(CH$_2$—C((CH$_2$)$_p$CH$_3$)H)$_m$—, —CH=CH—, or —C≡C—, wherein Y is O, S, Se, S—S, S(O), S(O)$_2$, m is 1-4 and p is 0-4.

Where more than one galactose moiety is present on the same ligand, the more than one galactose moieties may be linked to the oligonucleotide strand in a linear fashion, or, preferably, by a branched linker group. When connected in linear fashion, the galactose moieties may be attached to the linker group as side groups (i.e., every galactose moiety is attached to a linker group only at one point), and/or one or more of the galactose moieties may be interjected between linker groups (i.e., one or more galactose moieties are attached to linker groups at two points, e.g., via the C1 and the C6 positions).

Preferably, the linker group is a branched linker group, and more preferably a symmetric branched linker group. The branch point will be an at least trivalent, but may be a tetravalent, pentavalent, or hexavalent atom, or a group presenting such multiple valencies. In preferred embodiments, the branch point is a glycerol, or glycerol triphosphate, group. Preferred embodiments of branched linker groups are, for example, without limitation, those shown in FIG. 7.

In embodiments comprising more than one galactose moieties, the linker group(s) preferably provide for a certain distance between the galactose moieties, e.g., more than 5 Å, preferably more than 10 Å, more preferably more than 15 Å, or most preferably more than 20 Å. The distance between the galactose moieties may influence their ability to bind to and crosslink to more than one asialoglycoprotein receptor on the cell's surface.

RNA Strands

An RNAi agent of the invention includes a region of sufficient complementarity to the target gene, and is of sufficient length in terms of nucleotides, such that antisense strand may form a duplex with the target nucleic acid. The RNAi agent can modulate the function of the targeted molecule. For example, when the targeted molecule is an mRNA or pre-mRNA, the RNAi agent can inhibit gene expression; when the target is a microRNA (miRNA), the RNAi agent will inhibit the miRNA function and will thus up-regulate expression of the mRNAs targeted by the particular miRNA; when the target is a region of a pre-mRNA the affects splicing, the RNAi agent can alter the choice of splice site and thus the mRNA sequence; when the RNAi agent functions as an miRNA, expression of the targeted mRNA is inhibited.

A RNAi agent is, or includes, a region that is at least partially, and in some embodiments fully, complementary to the target RNA. It is not necessary that there be perfect complementarity between the RNAi agent and the target, but the correspondence must be sufficient to enable the RNAi agent, or a cleavage product thereof, to modulate (e.g., inhibit) target gene expression.

An RNAi agent will preferably have one or more of the following properties:
(1) it will be of the Formula 1, 2, 3, or 4 described below;
(2) it will have a 5' modification that includes one or more phosphate groups or one or more analogs of a phosphate group;
(3) it will, despite modifications, even to a very large number of bases specifically base pair and form a duplex structure with a homologous target RNA of sufficient thermodynamic stability to allow modulation of the activity of the targeted RNA;
(4) it will, despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, all of the nucleotide sugars can contain e.g., 2'OMe, 2' fluoro in place of 2' hydroxyl. Such agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_3$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. (Generally, it is preferred that a modified moiety at the 2' sugar position will be able to enter into hydrogen-bonding which is more characteristic of the 2'-OH moiety of a ribonucleotide than the 2'-H moiety of a deoxyribonucleotide. A preferred RNAi agent will: exhibit a $C_3$-endo pucker in all, or at least 50, 75, 80, 85, 90, or 95% of its sugars; exhibit a $C_3$-endo pucker in a sufficient amount of its sugars that it can give rise to a the RNA-characteristic A-family-type helix; will have no more than 20, 10, 5, 4, 3, 2, or 1 sugar which is not a $C_3$-endo pucker structure.

Preferred 2'-modifications with C3'-endo sugar pucker include: 2'-OH, 2'-O-Me, 2'-O-methoxyethyl, 2'-O-aminopropyl, 2'-F, 2'-O—CH$_2$—CO—NHMe, 2'-O—CH$_2$—CH$_2$—O—CH$_2$—CH$_2$—N(Me)$_2$, LNA (5) regardless of the nature of the modification, and even though the RNAi agent can contain deoxynucleotides or modified deoxynucleotides, it is preferred that DNA molecules, or any molecule in which more than 50, 60, or 70% of the nucleotides in the molecule are deoxyribonucleotides, or modified deoxyribonucleotides which are deoxy at the 2' position, are excluded from the definition of RNAi agent.

Preferred 2'-modifications with a C2'-endo sugar pucker include:
2'-H, 2'-Me, 2'-S-Me, 2'-Ethynyl, 2'-ara-F.

Sugar modifications can also include L-sugars and 2'-5'-linked sugars.

RNAi agents discussed herein include otherwise unmodified nucleotides as well as nucleotides that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (*Nucleic Acids Res.*, 1994, 22:2183-2196). Such rare or unusual RNAs, often termed modified RNAs, are typically the result of a post transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of all of the above are discussed herein.

As nucleic acids are polymers of subunits or monomers, many of the modifications described below occur at a position which is repeated within a nucleic acid, e.g., a modification of a base, or a phosphate moiety, or a non-linking O of a phosphate moiety. In some cases the modification will occur at all of the subject positions in the nucleic acid but in many, and infact in most cases it will not. By way of example, a modification may only occur at a 3' or 5' terminal position, may only occur in a terminal regions, e.g., at a position on a terminal nucleotide or in the last 2, 3, 4, 5, or 10 nucleotides of a strand. The ligand can be at attached at the 3' end, the 5' end, or at an internal position, or at a combination of these positions. For example, the ligand can be at the 3' end and the 5' end; at the 3' end and at one or more internal positions; at the 5' end and at one or more internal positions; or at the 3' end, the 5' end, and at one or more internal positions. E.g., a phosphorothioate modification at a non-linking O position may only occur at one or both termini, or may only occur in a terminal region, e.g., at a position on a terminal nucleotide or in the last 2, 3, 4, 5, or 10 nucleotides of the oligonucleotide. The 5' end can be phosphorylated.

Modifications and nucleotide surrogates are discussed below.

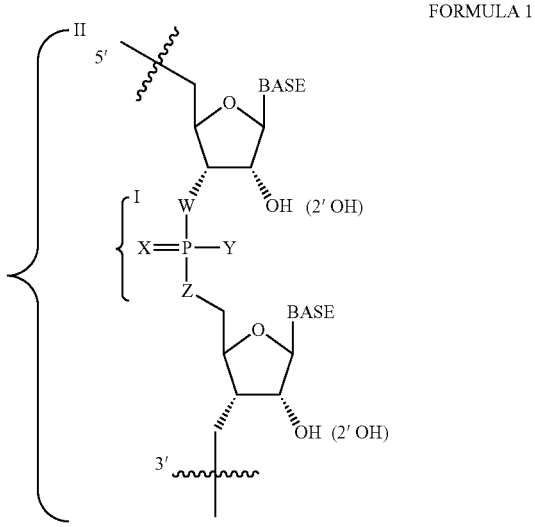

FORMULA 1

The scaffold presented above in Formula 1 represents a portion of a ribonucleic acid. The basic components are the ribose sugar, the base, the terminal phosphates, and phosphate internucleotide linkers. Where the bases are naturally occurring bases, e.g., adenine, uracil, guanine or cytosine, the sugars are the unmodified 2' hydroxyl ribose sugar (as depicted) and W, X, Y, and Z are all O, Formula 1 represents a naturally occurring unmodified oligoribonucleotide.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the above RNA components can confer improved properties, and, e.g., can render oligoribonucleotides more stable to nucleases. Unmodified oligoribonucleotides may also be less than optimal in terms of offering linker group points for attaching ligands or other moieties to an RNAi agent.

Modified nucleic acids and nucleotide surrogates can include one or more of:

(i) alteration, e.g., replacement, of one or both of the non-linking (X and Y) phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein.);

(ii) alteration, e.g., replacement, of a constituent of the ribose sugar, e.g., of the 2' hydroxyl on the ribose sugar, or wholesale replacement of the ribose sugar with a structure other than ribose, e.g., as described herein;

(iii) wholesale replacement of the phosphate moiety (bracket I) with "dephospho" linkers;

(iv) modification or replacement of a naturally occurring base;

(v) replacement or modification of the ribose-phosphate backbone (bracket II);

(vi) modification of the 3' end or 5' end of the RNA, e.g., removal, modification or replacement of a terminal phosphate group or conjugation of a moiety, e.g., a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid but rather modified simply indicates a difference from a naturally occurring molecule.

It is understood that the actual electronic structure of some chemical entities cannot be adequately represented by only one canonical form (i.e., Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species. For example, any phosphoroamidate (replacement of a nonlinking oxygen with nitrogen) would be represented by X=O and Y=N in the above figure.

Specific modifications are discussed in more detail below.

The Phosphate Group

The phosphate group is a negatively charged species. The charge is distributed equally over the two non-bridging oxygen atoms. However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged bridge or a charged bridge with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. Unlike the situation where only one of the non-bridging oxygens is altered, the phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both non-bridging oxygens which eliminate the chiral center, e.g., phosphorodithioate formation, may be desirable in that they cannot produce diastereomer mixtures. Thus, either or both of the non-bridging oxygens can be replaced by any one of S, Se, B, C, H, N, or OR (R is alkyl or aryl). Replacement with sulfur is preferred.

The phosphate bridge can also be modified by replacement of a bridging oxygen with nitrogen (bridged phosphoroamidates), sulfur (bridged phosphorothioates) and carbon (bridged methylenephosphonates). The replacement can occur at a terminal oxygen, e.g., at the 3'- or 5'-terminus. Replacement the 3'-terminus with carbon or the 5'-terminus with nitrogen is preferred.

Candidate agents can be evaluated for suitability as described below.

The Sugar Group

A modified RNA can include modification of all or some of the sugar groups of the ribonucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH$_2$CH$_2$O)$_n$CH$_2$CH$_2$OR; "locked" nucleic acids (LNA) in which the 2' hydroxyl is connected, e.g., by a methylene bridge or ethylene bridge (e.g., 2'-4'-ethylene bridged nucleic acid (ENA)), to the 4' carbon of the same ribose sugar; O-AMINE (AMINE=NH$_2$; alkylamino, dialkylamino, heterocyclyl, arylamino, diaryl amino, heteroaryl amino, or diheteroaryl amino, ethylene diamine, polyamino) and aminoalkoxy, O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), (OCH$_2$CH$_2$OCH$_3$, a PEG derivative), exhibit nuclease stabilities comparable to those modified with the robust phosphorothioate modification.

"Deoxy" modifications include hydrogen (i.e., deoxyribose sugars); halo (e.g., fluoro); amino (e.g., NH$_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH$_3$, 2'-O-allyl, 2'-C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNAs can also include "abasic" sugars, which lack a nucleobase at C-1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications. Chimeric oligonucleotides are well within the bounds of the present invention.

The modification can also entail the wholesale replacement of a ribose structure with another entity at one or more sites in the RNAi agent.

Candidate modifications can be evaluated as described below.

Replacement of the Phosphate Group

The phosphate group can be replaced by non-phosphorus containing connectors. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Candidate modifications can be evaluated as described below.

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g., nucleases). Again, while not wishing to be bound by theory, it can be desirable in some embodiment, to introduce alterations in which the bases are linker grouped by a neutral surrogate backbone.

Examples include the morphilino, cyclobutyl, pyrrolidine and peptide nucleic acid (PNA) nucleoside surrogates. A preferred surrogate is a PNA surrogate.

Candidate modifications can be evaluated as described below.

Terminal Modifications

The 3' and 5' ends of an oligonucleotide strand can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —($CH_2$)$_n$—, —($CH_2$)$_n$N—, —($CH_2$)$_n$O—, —($CH_2$)$_n$S—, O($CH_2CH_2O$)$_n$$CH_2CH_2$OH (e.g., n=3 or 6), abasic sugars, amide, carboxy, amine, oxyamine, oxyimine, thioether, disulfide, thiourea, sulfonamide, or morpholino, or biotin and fluorescein reagents. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipophilic oligonucleotide strands (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Preferred modifications include the addition of a methylphosphonate at the 3'-most terminal linkage; a 3' C5-aminoalkyl-dT; 3' cationic group; or another 3' conjugate to inhibit 3'-5' exonucleolytic degradation.

Terminal modifications useful for modulating activity include modification of the 5' end with phosphate or phosphate analogs. E.g., in preferred embodiments RNAi agents are 5' phosphorylated or include a phosphoryl analog at the 5' terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g., RP(OH)(O)—O-5'-, (OH)$_2$(O)P-5'-CH$_2$—), 5'-alkyletherphosphonates (R=alkylether=methoxymethyl (MeOCH$_2$—), ethoxymethyl, etc., e.g., RP(OH)(O)—O-5'-).

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include cholesterol. Terminal modifications can also be useful for cross-linking an RNAi agent to another moiety; modifications useful for this include mitomycin C.

Candidate modifications can be evaluated as described below.

The Bases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases" and "universal bases" can be employed. Examples include without limitation 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Generally, base changes are less preferred for promoting stability, but they can be useful for other reasons, e.g., some, e.g., 2,6-diaminopurine and 2 amino purine (e.g., 2-amino adenine), are fluorescent. Modified bases can reduce target specificity. This should be taken into consideration in the design of RNAi agents.

Candidate modifications can be evaluated as described below.

Evaluation of Candidate RNAi Agents

One can evaluate a candidate RNAi agent, e.g., a modified RNAi agent, for a selected property by exposing the agent or modified molecule and a control molecule to the appropriate conditions and evaluating for the presence of the selected property. For example, resistance to a degradent can be evaluated as follows. A candidate modified RNA (and preferably a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or serum, or a cellular fraction, e.g., a cell-free homogenate or disrupted cells. The candidate and control could then be evaluated for resistance to degradation by any of a number of approaches. For example, the candidate and control could be labeled, preferably prior to exposure, with, e.g., a radioactive or enzymatic label, or a fluorescent label, such as Cy3 or Cy5. Control and modified RNA's can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis or mass spectrometry can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to inhibit gene expression. For example, a cell, e.g., a mammalian cell, such as a mouse or human cell, can be co-transfected with a plasmid expressing a fluorescent protein, e.g., GFP, and a candidate RNAi agent homologous to the transcript encoding the fluorescent protein (see, e.g., WO 00/44914). For example, a modified RNAi agent homologous to the GFP mRNA can be assayed for the ability to inhibit GFP expression by monitoring for a decrease in cell fluorescence, as compared to a control cell, in which the transfection did not include the candidate RNAi agent, e.g., controls with no agent added and/or controls with a non-modified RNA added. Efficacy of the candidate agent on gene expression can be assessed by comparing cell fluorescence in the presence of the modified and unmodified RNAi agent. In an alternative functional assay, a candidate RNAi agent homologous to an endogenous mouse gene, preferably a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by an RNAi agent would cause the oocyte to exit metaphase arrest and initiate parthenogenetic development (Colledge et al. Nature 370: 65-68, 1994; Hashimoto et al. Nature, 370:68-71, 1994). The effect of the modified agent on target RNA levels can be verified by Northern blot to assay for a decrease in the level of target RNA, or by Western blot to assay for a decrease in the level of target protein, as compared to a negative control. Controls can include cells in which with no agent is added and/or cells in which a non-modified RNA is added.

An RNAi agent that targets an miRNA ore pre-miRNA can be assayed by monitoring expression of the transcript targeted by the miRNA. For example, an RNAi agent designed to bind an miRNA that targets GFP can be assessed by monitoring for an increase in cell fluorescence, as compared to a control cell, in which the transfection did not include the candidate RNAi agent, e.g., controls with no agent added and/or controls with a non-modified RNA added. In another example, an RNAi agent designed to bind an miRNA that targets an endogenous enzyme can be assessed by monitoring for an increase in enzyme activity, as compared to a control cell. The effect of the modified RNAi agent on target miRNA levels can be verified by Northern blot to assay for a decrease in the level of the target miRNA.

Exemplary Embodiments

One aspect the invention provides an RNAi agent for inhibiting the expression of a target gene in a cell, wherein the RNAi agent consists essentially of an oligoribonucleotide strand of between 15 and 30 nucleotides in length, wherein said oligoribonucleotide strand is coupled via a linker to a ligand of formula (I)

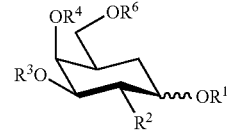

Formula (I)

wherein n is 1-20;

$R^1$, $R^3$, $R^4$ and $R^6$ are each independently for each occurrence H, a phosphate group, a ligand of formula (I), a $C_1$-$C_6$ alkyloxy, a $C_1$-$C_6$ acyloxy,

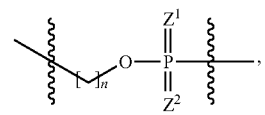

a carbohydrate or

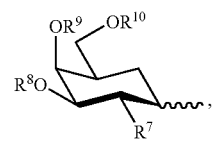

provided that at least one of $R^1$, $R^3$, $R^4$ and $R^6$ is

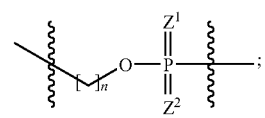

$R^2$ and $R^7$ are each independently for each occurrence OH or $NHCH_2COOH$;

$R^8$, $R^9$ and $R^{10}$ are independently for each occurrence H, a phosphate group, a ligand of formula (I), a $C_1$-$C_6$ alkyloxy, a $C_1$-$C_6$ acyloxy, a carbohydrate,

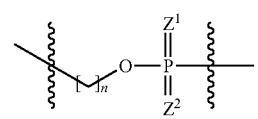

or

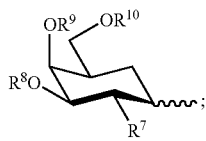

the linker is linear, branched, or a bond;

$Z^1$ and $Z^2$ are independently O, S, OH, O$^-$, OR$^{11}$, Se, BH$_3^-$, H, NHR$^{12}$, N(R$^{12}$)$_2$, optionally substituted alkyl, optionally substituted cycloalkyl, optionally substituted aralkyl, optionally substituted aryl, or optionally substituted heteroaryl;

$R^{11}$ and $R^{12}$ are each independently for each occurrence optionally substituted alkyl, optionally substituted cycloalkyl, optionally substituted aryl, optionally substituted aralkyl, optionally substituted heterocyclyl, optionally substituted heteroaryl or amino acid;

wherein said oligoribonucleotide strand is complementary to at least one portion of an mRNA corresponding to the target gene.

In one embodiment $R^1$, $R^3$, $R^4$ and $R^6$ are each independently for each occurrence H, a phosphate group, a ligand of formula (I), a C$_1$-C$_6$ alkyloxy, a C$_1$-C$_6$ acyloxy or

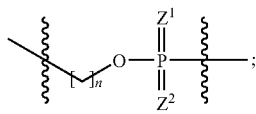

and $Z^1$ and $Z^2$ are independently O or S.

In a preferred embodiment the formula (I) has the structure

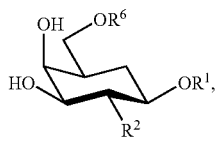

wherein $R^6$ is H, a phosphate group, or a ligand of formula (I) and $R^1$ is

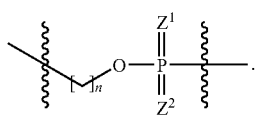

In one embodiment the branched linker has a structure of formula (III)

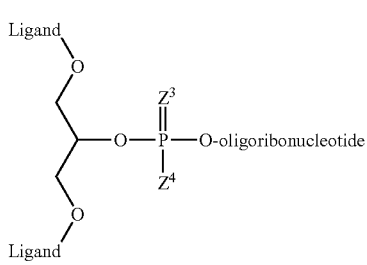

Formula (III)

wherein $Z^3$ and $Z^4$ are independently independently O, S, OH, O$^-$, OR$^{11}$, Se, BH$_3^-$, H, NHR$^{12}$, N(R$^{12}$)$_2$, optionally substituted alkyl, optionally substituted cycloalkyl, optionally substituted aralkyl, optionally substituted aryl, or optionally substituted heteroaryl;

$R^{11}$ and $R^{12}$ are each independently for each occurrence optionally substituted alkyl, optionally substituted cycloalkyl, optionally substituted aryl, optionally substituted aralkyl, optionally substituted heterocyclyl, optionally substituted heteroaryl or amino acid. In a preferred embodiment, $Z^3$ and $Z^4$ are independently O or S.

In one embodiment, the intervening linker has a structure of formula (IV)

Formula (IV)

wherein n is 1-20; and $Z^5$ and $Z^6$ are each independently independently O, S, OH, O$^-$, OR$^{11}$, Se, BH$_3^-$, H, NHR$^{12}$, N(R$^{12}$)$_2$, optionally substituted alkyl, optionally substituted cycloalkyl, optionally substituted aralkyl, optionally substituted aryl, or optionally substituted heteroaryl;

$R^{11}$ and $R^{12}$ are each independently for each occurrence optionally substituted alkyl, optionally substituted cycloalkyl, optionally substituted aryl, optionally substituted aralkyl, optionally substituted heterocyclyl, optionally substituted heteroaryl or amino acid. In a preferred embodiment $Z^5$ and $Z^6$ are independently O or S.

In certain embodiments, the present invention relates to the aforementioned RNAi agent, wherein n is 3. In certain embodiments, the present invention relates to the aforementioned RNAi agent, wherein at least one of $Z^5$ and $Z^6$ is S. In certain embodiments, the present invention relates to the aforementioned RNAi agent, wherein both of $Z^5$ and $Z^6$ are O.

In certain embodiments, the present invention relates to the aforementioned RNAi agent, wherein the distance between the galactose moieties is at least about 4 Å, at least about 10 Å, at least about 15 Å, or at least about 20 Å.

In certain embodiments, the present invention relates to the aforementioned RNAi agent, wherein the RNAi agent is capable of inhibiting the expression of the target gene in the cell.

In certain embodiments, the present invention relates to the aforementioned RNAi agent, wherein the cell harbors an asialoglycoprotein receptor on its surface.

In certain embodiments, the present invention relates to the aforementioned RNAi agent, wherein the cell is a hepatocyte.

Another aspect of the invention provides an RNAi agent for inhibiting the expression of a target gene in a cell, wherein the RNAi agent consists essentially of two mutually complementary oligoribonucleotide strands of between 15 and 30 nucleotides in length, wherein at least one of the oligoribonucleotide strands is coupled via a linker to a ligand of formula (I)

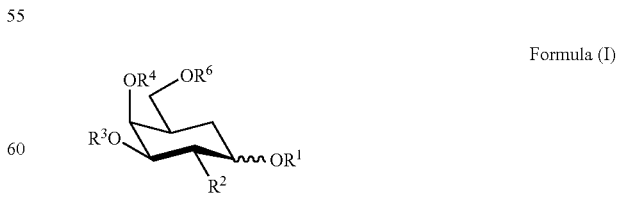

Formula (I)

wherein n is 1-20;

$R^1$, $R^3$, $R^4$ and $R^6$ are each independently for each occurrence H, a phosphate group, a ligand of formula (I), a C$_1$-C$_6$ alkyloxy, a C$_1$-C$_6$ acyloxy,

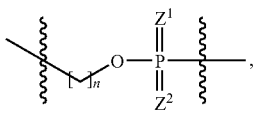

a carbohydrate or

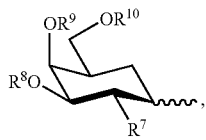

provided that at least one of $R^1$, $R^3$, $R^4$ and $R^6$ is

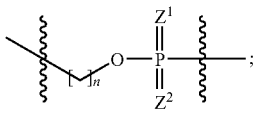

$R^2$ and $R^7$ are each independently for each occurrence OH or $NHCH_2COOH$;

$R^8$, $R^9$ and $R^{10}$ are independently for each occurrence H, a phosphate group, a ligand of formula (I), a $C_1$-$C_6$ alkyloxy, a $C_1$-$C_6$ acyloxy,

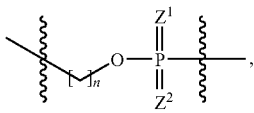

a carbohydrate or

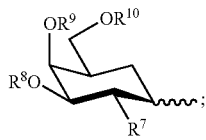

the linker is linear, branched, or a bond;

$Z^1$ and $Z^2$ are independently O, S, OH, O−, $OR^{11}$, Se, BH3−, H, $NHR^{12}$, $N(R^{12})_2$, optionally substituted alkyl, optionally substituted cycloalkyl, optionally substituted aralkyl, optionally substituted aryl, or optionally substituted heteroaryl;

$R^{11}$ and $R^{12}$ are each independently for each occurrence optionally substituted alkyl, optionally substituted cycloalkyl, optionally substituted aryl, optionally substituted aralkyl, optionally substituted heterocyclyl, optionally substituted heteroaryl or amino acid;

wherein at least one oligoribonucleotide strand is complementary to at least one portion of an mRNA corresponding to the target gene.

In one embodiment $R^1$, $R^3$, $R^4$ and $R^6$ are each independently for each occurrence H, a phosphate group, a ligand of formula (I), a $C_1$-$C_6$ alkyloxy, a $C_1$-$C_6$ acyloxy or

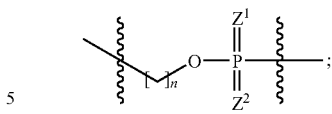

and $Z^1$ and $Z^2$ are independently O or S.

In a preferred embodiment the formula (I) has the structure

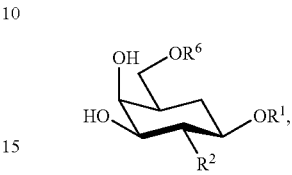

wherein $R^6$ is H, a phosphate group, or a ligand of formula (I) and $R^1$ is

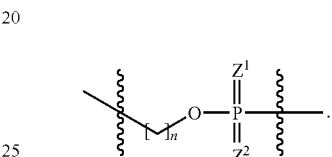

In one embodiment the branched linker has a structure of formula (III)

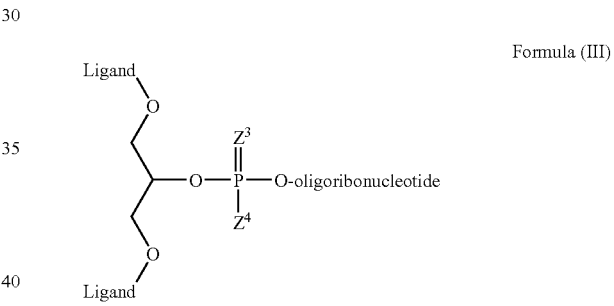

Formula (III)

wherein $Z^3$ and $Z^4$ are independently independently O, S, OH, O−, $OR^{11}$, Se, BH3−, H, $NHR^{12}$, $N(R^{12})_2$, optionally substituted alkyl, optionally substituted cycloalkyl, optionally substituted aralkyl, optionally substituted aryl, or optionally substituted heteroaryl;

$R^{11}$ and $R^{12}$ are each independently for each occurrence optionally substituted alkyl, optionally substituted cycloalkyl, optionally substituted aryl, optionally substituted aralkyl, optionally substituted heterocyclyl, optionally substituted heteroaryl or amino acid. In a preferred embodiment, $Z^3$ and $Z^4$ are independently O or S.

In one embodiment, the intervening linker has a structure of formula (IV)

ligand-O—$CH_2CH_2(OCH_2CH_2)_n$OP($Z^5$)($Z^6$)O-branched-linker     Formula (IV)

wherein n is 1-20; and $Z^5$ and $Z^6$ are each independently independently O, S, OH, O−, $OR^{11}$, Se, BH3-, H, $NHR^{12}$, $N(R^{12})_2$, optionally substituted alkyl, optionally substituted cycloalkyl, optionally substituted aralkyl, optionally substituted aryl, or optionally substituted heteroaryl;

$R^{11}$ and $R^{12}$ are each independently for each occurrence optionally substituted alkyl, optionally substituted cycloalkyl, optionally substituted aryl, optionally substituted aralkyl, optionally substituted heterocyclyl, optionally substituted heteroaryl or amino acid. In a preferred embodiment $Z^5$ and $Z^6$ are independently O or S.

In certain embodiments, the present invention relates to the aforementioned RNAi agent, wherein n is 3. In certain embodiments, the present invention relates to the aforementioned RNAi agent, wherein at least one of $Z^5$ and $Z^6$ is S. In certain embodiments, the present invention relates to the aforementioned RNAi agent, wherein both of $Z^5$ and $Z^6$ are O.

In certain embodiments, the present invention relates to the aforementioned RNAi agent, wherein the distance between the galactose moieties is at least about 4 Å, at least about 10 Å, at least about 15 Å, or at least about 20 Å.

In certain embodiments, the present invention relates to the aforementioned RNAi agent, wherein the RNAi agent is capable of inhibiting the expression of the target gene in the cell.

In certain embodiments, the present invention relates to the aforementioned RNAi agent, wherein the cell harbors an asialoglycoprotein receptor on its surface.

In certain embodiments, the present invention relates to the aforementioned RNAi agent, wherein the cell is a hepatocyte.

In certain embodiments, the present invention relates to any one of the aforementioned RNAi agents, wherein n is 1, 2, 3, 4, 5 or 6.

In certain embodiments, the present invention relates to any one of the aforementioned RNAi agents, wherein n is 4.

In certain embodiments, the present invention relates to any one of the aforementioned RNAi agents, wherein at least one of $Z^1$ and $Z^2$ is S.

In certain embodiments, the present invention relates to any one of the aforementioned RNAi agents, wherein both of $Z^1$ and $Z^2$ are O.

In certain embodiments, the present invention relates to any one of the aforementioned RNAi agents, wherein at least one the oligoribonucleotide strands comprises at least one phosphorothioate linkage.

In certain embodiments, the present invention relates to any one of the aforementioned RNAi agents, wherein at least one of the oligoribonucleotide strands comprises at least one nucleotide with a 2'-modification. In certain embodiments, the present invention relates to any one of the aforementioned RNAi agents, wherein the 2'-modification comprises one of 2'-H, 2'-O-methyl, 2'-O-methoxyethyl, 2'-O-aminopropyl, 2'-Fluoro, 2'-O—$CH_2$—CO—NHMe, 2'-O—$CH_2CH_2OCH_2CH_2N(Me)_2$, 2'-4'-methylene (LNA), 2'-4'-ethylene (ENA), 2'-S-methyl, 2'-ara-fluoro, 2'-O-allyl, 2'-C-allyl, 2'-O—$NH_2$, 2'—$NH_2$ and 2'-ethynyl.

Another aspect of the invention relates to a pharmaceutical composition, comprising (i) any one of the aforementioned RNAi agents; and (ii) a pharmaceutically acceptable excipient.

Another aspect of the invention relates to a method for the manufacture of an RNAi agent of any one of the aforementioned RNAi agents, comprising the steps of (i) synthesizing two mutually complementary oligoribonucleotide strands of between 15 and 30 nucleotides in length, wherein at least one of the oligoribonucleotides is coupled to a ligand comprising a linker group and at least one galactose moiety; and (ii) effecting the hybridization of the at least two mutually complementary oligoribonucleotides. In certain embodiments, the present invention relates to the aforementioned method of manufacture, further comprising the step of formulating the RNAi agent with a pharmaceutically acceptable excipient.

Another aspect of the invention relates to a method to introduce an RNAi agent into a cell, comprising the step of contacting the cell with the RNAi agent of the present invention. In certain embodiments, the cell is a hepatocyte.

Another aspect of the invention relates to a method of treatment, comprising a step of administering to a subject in need thereof a therapeutically effective amount of a pharmaceutical composition of the present invention. In certain embodiments, the subject is in need of a treatment for a disease or condition related to unwanted expression of a target gene in the liver. In certain embodiments, the subject is a vertebrate, mammal, or human.

Another aspect of the invention relates to a cell, comprising an RNAi agent of the present invention. In certain embodiments, the cell is a hepatocyte.

Methods for Making Oligonucleotide Agents

A listing of ribonucleosides containing the ribonucleosides described herein are described in "The RNA Modification Database" maintained by Pamela F. Crain, Jef Rozenski and James A. McCloskey; Departments of Medicinal Chemistry and Biochemistry, University of Utah, Salt Lake City, Utah 84112, USA.

The 5' silyl protecting group can be used in conjunction with acid labile orthoesters at the 2' position of ribonucleosides to synthesize oligonucleotides via phosphoramidite chemistry. Final deprotection conditions are known not to significantly degrade RNA products. Functional groups on the unusual and universal bases are blocked during oligonucleotide synthesis with protecting groups that are compatible with the operations being performed that are described herein. All syntheses can be conducted in any automated or manual synthesizer on large, medium, or small scale. The syntheses may also be carried out in multiple well plates or glass slides.

The 5'-O-silyl group can be removed via exposure to fluoride ions, which can include any source of fluoride ion, e.g., those salts containing fluoride ion paired with inorganic counterions e.g., cesium fluoride and potassium fluoride or those salts containing fluoride ion paired with an organic counterion, e.g., a tetraalkylammonium fluoride. A crown ether catalyst can be utilized in combination with the inorganic fluoride in the deprotection reaction. Preferred fluoride ion source are tetrabutylammonium fluoride or aminehydrofluorides (e.g., combining aqueous HF with triethylamine in a dipolar aprotic solvent, e.g., dimethylformamide).

The choice of protecting groups for use on the phosphite triesters and phosphotriesters can alter the stability of the triesters towards fluoride. Methyl protection of the phosphotriester or phosphitetriester can stabilize the linkage against fluoride ions and improve process yields.

Since ribonucleosides have a reactive 2' hydroxyl substituent, it can be desirable to protect the reactive 2' position in RNA with a protecting group that is compatible with a 5'-O-silyl protecting group, e.g., one stable to fluoride. Orthoesters meet this criterion and can be readily removed in a final acid deprotection step that can result in minimal RNA degradation.

Tetrazole catalysts can be used in the standard phosphoramidite coupling reaction. Preferred catalysts include e.g., tetrazole, S-ethyl-tetrazole, p-nitrophenyltetrazole.

The general process is as follows. Nucleosides are suitably protected and functionalized for use in solid-phase or solution-phase synthesis of RNA oligonucleotides. The 2'-hydroxyl group in a ribonucleotide can be modified using a tris orthoester reagent. The 2'-hydroxyl can be modified to yield a 2'-O-orthoester nucleoside by reacting the ribonucleoside with the tris orthoester reagent in the presence of an acidic catalyst, e.g., pyridinium p-toluene sulfonate. This reaction is known to those skilled in the art. The product can then be subjected to further protecting group reactions (e.g., 5'-O-silylation) and functionalizations (e.g., 3'-O-phosphitylation) to produce a desired reagent (e.g., nucleoside phosphoramidite) for incorporation within an oligonucleotide or polymer by reactions known to those skilled in the art.

Preferred orthoesters include those comprising ethylene glycol ligands which are protected with acyl or ester protecting groups. Specifically, the preferred acyl group is acetyl. The nucleoside reagents may then be used by those skilled in the art to synthesize RNA oligonucleotides on commercially available synthesizer instruments, e.g., Gene Assembler Plus (Pharmacia), 380B (Applied Biosystems). Following synthesis (either solution-phase or solid-phase) of an oligonucleotide or polymer, the product can be subjected to one or more reactions using non-acidic reagents. One of these reactions may be strong basic conditions, for example, 40% methylamine in water for 10 minutes at 55° C., which will remove the acyl protecting groups from the ethylene glycol ligands but leave the orthoester moiety attached. The resultant orthoester may be left attached when the polymer or oligonucleotide is used in subsequent applications, or it may be removed in a final mildly-acidic reaction, for example, 10 minutes at 55° C. in 50 mM acetic acid, pH 3.0, followed by addition of equal volume of 150 mM TRIS buffer for 10 minutes at 55° C.

Universal bases are described in "Survey and Summary: The Applications of Universal DNA base analogues" Loakes, D., *Nucleic Acid Research* 2001, 29, 2437, which is incorporated by reference in its entirety. Specific examples are described in the following: Liu, D.; Moran, S.; Kool, E. T. *Chem. Biol.,* 1997, 4, 919-926; Morales, J. C.; Kool, E. T. *Biochemistry,* 2000, 39, 2626-2632; Matray, T, J.; Kool, E. T. *J. Am. Chem. Soc.,* 1998, 120, 6191-6192; Moran, S. Ren, R. X.-F.; Rumney IV, S.; Kool, E. T. *J. Am. Chem. Soc.,* 1997, 119, 2056-2057; Guckian, K. M.; Morales, J. C.; Kool, E. T. *J. Org. Chem.,* 1998, 63, 9652-9656; Berger, M.; Wu. Y.; Ogawa, A. K.; McMinn, D. L.; Schultz, P. G.; Romesberg, F. E. *Nucleic Acids Res.,* 2000, 28, 2911-2914; Ogawa, A. K.; Wu, Y.; McMinn, D. L.; Liu, J.; Schultz, P. G.; Romesberg, F. E. *J. Am. Chem. Soc.,* 2000, 122, 3274-3287; Ogawa, A. K.; Wu. Y.; Berger, M.; Schultz, P. G.; Romesberg, F. E. *J. Am. Chem. Soc.,* 2000, 122, 8803-8804; Tae, E. L.; Wu, Y.; Xia, G.; Schultz, P. G.; Romesberg, F. E. *J. Am. Chem. Soc.,* 2001, 123, 7439-7440; Wu, Y.; Ogawa, A. K.; Berger, M.; McMinn, D. L.; Schultz, P. G.; Romesberg, F. E. *J. Am. Chem. Soc.,* 2000, 122, 7621-7632; McMinn, D. L.; Ogawa. A. K.; Wu, Y.; Liu, J.; Schultz, P. G.; Romesberg, F. E. *J. Am. Chem. Soc.,* 1999, 121, 11585-11586; Brotschi, C.; Haberli, A.; Leumann, C, J. *Angew. Chem. Int. Ed.,* 2001, 40, 3012-3014; Weizman, H.; Tor, Y. *J. Am. Chem. Soc.,* 2001, 123, 3375-3376; Lan, T.; McLaughlin, L. W. *J. Am. Chem. Soc.,* 2000, 122, 6512-13.

As discussed above, the monomers and methods described herein can be used in the preparation of modified RNA molecules, or polymeric molecules comprising any combination of monomer compounds described herein and/or natural or modified ribonucleotides. Modified RNA molecules include e.g., those molecules containing a chemically or stereochemically modified nucleoside (e.g., having one or more backbone modifications, e.g., phosphorothioate or P-alkyl; having one or more sugar modifications, e.g., 2'-$OCH_3$ or 2'-F; and/or having one or more base modifications, e.g., 5-alkylamino or 5-allylamino) or a nucleoside surrogate.

Coupling of 5'-hydroxyl groups with phosphoramidites forms phosphite ester intermediates, which in turn are oxidized e.g., with iodine, to the phosphate diester. Alternatively, the phosphites may be treated with, e.g., sulfur, selenium, amino, and boron reagents to form modified phosphate backbones. Linkages between the monomers described herein and a nucleoside or oligonucleotide chain can also be treated with iodine, sulfur, selenium, amino, and boron reagents to form unmodified and modified phosphate backbones respectively. Similarly, the monomers described herein may be coupled with nucleosides or oligonucleotides containing any of the modifications or nucleoside surrogates described herein.

The synthesis and purification of oligonucleotide conjugates can be performed by established methods. See, for example, Trufert et al., Tetrahedron, 52:3005, 1996; and Manoharan, "Oligonucleotide Conjugates in Antisense Technology," in *Antisense Drug Technology*, ed. S. T. Crooke, Marcel Dekker, Inc., 2001. The protected monomer compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Other synthetic chemistry transformations, protecting groups (e.g., for hydroxyl, amino, etc. present on the bases) and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. *Fieser, Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The protected monomer compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds described herein can also contain linkages (e.g., carbon-carbon bonds, carbon-nitrogen bonds, e.g., amides) or substituents that can restrict bond rotation, e.g., restriction resulting from the presence of a ring or double bond. Accordingly, all cis/trans, E/Z isomers, and rotational isomers (rotamers) are expressly included herein. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Formulation

The RNAi agents described herein can be formulated for administration to a subject.

For ease of exposition the formulations, compositions and methods in this section are discussed largely with regard to unmodified RNAi agents. It should be understood, however, that these formulations, compositions and methods can be practiced with other RNAi agents, e.g., modified RNAi agents, and such practice is within the invention.

A formulated RNAi agent composition can assume a variety of states. In some examples, the composition is at least partially crystalline, uniformly crystalline, and/or anhydrous (e.g., less than 80, 50, 30, 20, or 10% water). In another example, the RNAi agent is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the RNAi agent composition is formulated in a manner that is compatible with the intended method of administration (see, below).

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An RNAi agent preparation can be formulated in combination with another agent, e.g., another therapeutic agent or an agent that stabilizes an RNAi agent, e.g., a protein that complexes with an RNAi agent. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the RNAi agent preparation includes a second RNAi agent, e.g., a second RNAi agent that can modulate gene expression with respect to a second gene, or with respect to the same gene. Still other preparation can include at least three, five, ten, twenty, fifty, or a hundred or more different RNAi agent species. Such RNAi agents can modulate gene expression with respect to a similar number of different genes.

In one embodiment, the RNAi agent preparation includes at least a second therapeutic agent (e.g., an agent other than an RNA or a DNA). For example, an RNAi agent composition for the treatment of a viral disease, e.g., HCV, might include a known antiviral agent (e.g., a protease inhibitor). In another example, an RNAi agent composition for the treatment of a cancer might further comprise a chemotherapeutic agent. In a preferred embodiment, the pharmaceutical composition includes an additive that stimulates the expression, activity and/or affinity of the asialoglycoprotein receptor for the binding of the RNAi agent. For example, the additive may result in an increase of the calcium concentrations in the liver. An increased calcium concentration in the liver may enhance the expression of the asialoglycoprotein receptor, and increase the number of receptor molecules present on hepatocytes as compared to a delivery of the RNAi agent without the additive.

RNAi agents described herein can be formulated for delivery in a membranous molecular assembly, e.g., a liposome or a micelle. In one embodiment, a preparation including an RNAi agent can be formulated as an emulsion that includes a surfactant.

Targeting to the Liver

Aspects of the invention relate to silencing genes expressed in the liver, or to upregulating genes that are regulated by one or more endogenous miRNAs. Accordingly, the invention includes compositions and methods for delivering RNAi agents to the liver, e.g., to treat disorders of or related to the liver.

An RNAi agent composition of the invention can be one that has been modified to alter distribution in favor of the liver. A composition of the invention includes an RNAi agent, e.g., an RNAi agent described herein.

Preferably, an RNAi agent of the invention is designed to be effective as a treatment for one or more adverse conditions or diseases of the liver, e.g., Alagille syndrome, alcoholic liver disease, alpha-1-antitrypsin deficiency, Budd-Chiari syndrome, biliary atresia, Byler disease, dyslipidemias, Carol i-disease, Crigler-Najjar Syndrome, Dubin-Johnson Syndrome, fatty liver, galactosemia, Gilbert syndrome, glycogen storage disease 1, hemangioma, hemochromatosis, hepatitis of viral or autoimmune etiology, liver cancer, liver fibrosis and cirrhosis, porphyria cutanea tarda, erythrohepatic protoporphyria, Rotor syndrome, sclerosing cholangitis, or Wilson disease.

For example, an RNAi agent directed to the liver can target apoB-100 to treat a disorder characterized by elevated or otherwise unwanted expression of apoB-100, elevated or otherwise unwanted levels of cholesterol, and/or disregulation of lipid metabolism. The RNAi agent can be administered to an individual at risk for the disorder to delay onset of the disorder or a symptom of the disorder. These disorders include HDL/LDL cholesterol imbalance; dyslipidemias, e.g., familial combined hyperlipidemia (FCHL), acquired hyperlipidemia; hypercholestorolemia; statin-resistant hypercholesterolemia; coronary artery disease (CAD) coronary heart disease (CHD) atherosclerosis. In one embodiment, the RNAi agent that targets apoB-100 is administered to a subject diagnosed as having statin-resistant hypercholesterolemia.

The apoB-100 RNAi agent can be administered in an amount sufficient to reduce levels of serum LDL-C and/or HDL-C and/or total cholesterol in a subject. In one embodiment, the RNAi agent is administered in an amount sufficient to reduce the risk of myocardial infarction the subject.

In one embodiment, expression levels of apoB-100 are decreased in the liver following administration of the apoB-100 RNAi agent. For example, the RNAi agent can be complexed with a moiety that targets the liver, e.g., an antibody or ligand that binds a receptor on the liver.

In other embodiments, an RNAi agent targeted to the liver can modulate expression of, e.g., beta-catenin or glucose-6-phosphatase RNA, to treat a liver-related disorder.

In another embodiment, the RNAi agent targets an miRNA or pre-miRNA expressed in the liver. In another embodiment, the human is suffering from a disorder characterized by overexpression or accumulation of the miRNA in the liver, or decreased expression of a nucleic acid that is the target of the miRNA expressed in the liver. Administration of the RNAi agent to the subject, or to a cell of the lung of the subject, can result in the pairing of the RNAi agent with the target miRNA and the subsequent downregulation of the miRNA.

In one embodiment, the RNAi agent targets an miRNA normally expressed in liver tissue, and in another embodiment, the human is suffering from a disorder characterized by decreased expression of the miRNA in the liver. Administration of the RNAi agent to the subject, or to a cell of the liver, at least partially rescues the function of the downregulated miRNA.

In one embodiment, the RNAi agent targets an RNA that is the product of a gene from a pathogenic organism. For example, a hepatocyte infected with any of a number of hepatitis viruses, e.g., hepatitis A, B or C, will produce various RNAs and proteins from the viral genome that relate to viral replication.

In one embodiment, the RNAi agent targets a gene related to the formation of fibrotic lesions in the liver, e.g., a gene related to the formation of the extracellular matrix, e.g., a collagen gene.

In one embodiment, the RNAi agent targets a gene related to the development and progression of cancer, e.g., of liver cancer, e.g., of hepatocellular carcinoma. For example, a gene essential for the proliferation of cells may be targeted, for example, without limitation, a gene involved in the formation of the mitotic spindle, or a gene that inhibits the apoptosis of cancer cells, e.g., bcl-2.

Finally, the present invention also provides the use of an RNAi agent according to the invention for the preparation of a pharmaceutical composition for curative, preventive or vaccine treatment of mammals. Preferably, such compositions are intended for the treatment of the human or animal body. "Treatment" as used herein refers to prophylaxis and therapy. It concerns both the treatment of humans and animals. A "therapeutically effective amount of a peptide or a composition" is a dose sufficient for the alleviation of one or more symptoms normally associated with the disease desired to be treated. A method according to the invention is preferentially intended for the treatment of the diseases listed above.

Route of Delivery

The RNAi agents described herein can be administered by various routes of delivery, e.g., by oral, pulmonary, intravenous, topical, rectal, anal, or vaginal, delivery, e.g., as described in International Application Serial No. PCT/US2004/11829, filed Apr. 16, 2004. The contents of this reference are incorporated herein in their entirety.

Dosage

In one aspect, the invention features a method of administering an RNAi agent to a subject (e.g., a human subject). The method includes administering a unit dose of the RNAi agent that targets an RNA, e.g., an mRNA, in the subject (e.g., an endogenous or pathogen target RNA). In one embodiment, the unit dose is less than 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNAi agent (e.g., about $4.4 \times 10^{16}$ copies) per kg of bodyweight, or less than 1500, 750, 300, 150, 75,15, 7.5, 1.5, 0.75, 0.15, 0.075, 0.015, 0.0075, 0.0015, 0.00075, 0.00015 nmole of RNAi agent per kg of bodyweight.

The defined amount can be an amount effective to treat or prevent a disease or disorder, e.g., a disease or disorder associated with the target RNA, such as an RNA present in the liver. The unit dose, for example, can be administered by injection (e.g., intravenous or intramuscular), an inhaled dose, or a topical application. Particularly preferred dosages are less than 2,1, or 0.1 mg/kg of body weight.

In a preferred embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities. In one embodiment, the subject has a viral infection and the modality is an antiviral agent other than an RNAi agent. In another embodiment, the subject has atherosclerosis and the effective dose of an RNAi agent is administered in combination with, e.g., after surgical intervention, e.g., angioplasty.

In one embodiment, a subject is administered an initial dose and one or more maintenance doses of an RNAi agent, or a precursor, e.g., a larger RNAi agent which can be processed into an RNAi agent. The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time, which will vary depending upon the nature of the particular disease, its severity and the overall condition of the patient. In preferred embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the RNAi agent pharmaceutical composition includes a plurality of RNAi agent species. In another embodiment, the RNAi agent species has sequences that are non-overlapping and non-adjacent to another species with respect to a naturally occurring target sequence. In another embodiment, the plurality of RNAi agent species is specific for different naturally occurring target genes. In another embodiment, the RNAi agent is allele specific.

In some cases, a patient is treated with an RNAi agent in conjunction with other therapeutic modalities. For example, a patient being treated for a liver disease, e.g., early stage hepatocellular carcinoma, can be administered an RNAi agent specific for a target gene known to enhance the progression of the disease in conjunction with a drug known to inhibit activity of the target gene product. For example, a patient who has early stage hepatocellular carcinoma can be treated with an RNAi agent that targets, for example, bcl-2, or a gene involved in DNA adduct repair, in conjunction with the small molecule cisplatin, which is known to form DNA adducts, primarily intrastrand crosslink adducts (See Siddikh, Oncogene. 2003, 22:7265).

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107, 094).

The concentration of the RNAi agent composition is an amount sufficient to be effective in treating or preventing a disorder or to regulate a physiological condition in humans. The concentration or amount of RNAi agent administered will depend on the parameters determined for the agent and the method of administration, e.g., oral, nasal, buccal, pulmonary, intravenous, or rectal delivery. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an RNAi agent, e.g., a double-stranded RNAi agent, or precursor thereof) can include a single treatment or, preferably, can include a series of treatments. It will also be appreciated that the effective dosage of an RNAi agent used for treatment may increase or decrease over the course of a particular treatment. Changes in dosage may result and become apparent from the results of diagnostic assays as described herein. For example, the subject can be monitored after administering an RNAi agent composition. Based on information from the monitoring, an additional amount of the RNAi agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on $EC_{50}$ found to be effective in in vitro and in vivo animal models. In some embodiments, the animal models include transgenic animals that express a human gene, e.g., a gene that produces a target RNA. The transgenic animal can be deficient for the corresponding endogenous RNA. In another embodiment, the composition for testing includes an RNAi agent that is complementary, at least in an internal region, to a sequence that is conserved between the target RNA in the animal model and the target RNA in a human.

In one aspect, the invention features a method that includes: administering a first amount of a composition that comprises an RNAi agent, e.g., a double-stranded RNAi agent or precursor thereof) to a subject, wherein the RNAi agent is substantially complementary to a target nucleic acid; evaluating an activity associated with a protein encoded by the target nucleic acid; wherein the evaluation is used to determine if a second amount should be administered. In a preferred embodiment the method includes administering a second amount of the composition, wherein the timing of administration or dosage of the second amount is a function of the evaluating. The method can include other features described herein.

In another aspect, the invention features a method of administering a source of an RNAi agent to a subject. The method includes administering or implanting a source of an RNAi agent. In one embodiment, the source releases the RNAi agent over time, e.g., the source is a controlled or a slow release source, e.g., a microparticle that gradually releases the RNAi agent. In another embodiment, the source is a pump, e.g., a pump that includes a sensor or a pump that can release one or more unit doses.

In one aspect, the invention features a pharmaceutical composition that includes an RNAi agent, including a nucleotide sequence sufficiently complementary to a target RNA to allow duplex formation with a target nucleic acid. The target RNA can be a transcript of an endogenous human gene. In one embodiment, the RNAi agent (a) is about 5 to about 100 nucleobases long, e.g., about 8 to about 75, e.g., about 8 to about 50 nucleotides long, e.g., about 15 to about 30 nucleotides long, e.g., 15,16, 17, 18, 19, 20, 21, 22, 23, 24, or 25 nucleotides; and (b) is complementary to an endogenous target RNA In one embodiment, the pharmaceutical composition can be an emulsion, microemulsion, cream, jelly, or liposome.

In certain other aspects, the invention provides kits that include a suitable container containing a pharmaceutical formulation of an RNAi agent or a precursor of an RNAi agent). In certain embodiments the individual components of the pharmaceutical formulation may be provided in one container. Alternatively, it may be desirable to provide the components of the pharmaceutical formulation separately in two or more containers, e.g., one container for a preparation comprising one strand of the RNAi agent, and at least another for the second strand. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

In another aspect, the invention features a device, e.g., an implantable device, wherein the device can dispense or administer a composition that includes an RNAi agent, or a precursor, e.g., a larger RNAi agent which can be processed into an RNAi agent. The RNAi agent can inhibit expression of an endogenous transcript. In one embodiment, the device is coated with the composition. In another embodiment the RNAi agent is disposed within the device. In another embodiment, the device includes a mechanism to dispense a unit dose of the composition. In other embodiments the device releases the composition continuously, e.g., by diffusion. Exemplary devices include stents, catheters, pumps, artificial organs or organ components (e.g., artificial heart, a heart valve, etc.), and sutures.

Cells Comprising an RNAi Agent of the Invention

The invention further concerns a cell comprising an RNAi agent of the invention. Preferred embodiments of the instant cell are as provided for other inventive aspects above. According to the invention, "cells" include prokaryotic cells and eukaryotic cells, yeast cells, plant cells, human or animal cells, in particular mammalian cells. In a preferred embodiment, the cell is a hepatocyte. In particular, cancer cells should be mentioned. In preferred embodiments, the cell will be a cell expressing the asialoglyprotein receptor, such as a hepatocyte, preferably of mammalian, and more preferably of human, origin.

Remarks

These and other embodiments are disclosed or are obvious from and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on Internet, e.g., under http://www.ncbi.nlm.nih.gov/PubMed/medline.html. Further databases and addresses, such as http://www.ncbi.nlm.nih.gov, http://www.infobiogen.fr, http://www.fmi.ch/biology/research$_1$3 tools.html, http://www.tigr.org, are known to the person skilled in the art and can also be obtained using, e.g., http://www.lycos.com. An overview of patent information in biotechnology and a survey of relevant sources of patent information useful for retrospective searching and for current awareness is given in Berks, TIBTECH 12 (1994), 352-364.

The methods, compositions and uses of the invention can be applied in the treatment of all kinds of diseases the treatment and/or diagnostic of which is related to or dependent on the transfer of nucleic acids in cells. The compositions, and uses of the present invention may be desirably employed in humans, although animal treatment is also encompassed by the uses described herein.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced different from what is specifically described herein.

The disclosure of all patents, publications, published patent applications, and database entries cited in the present application are hereby incorporated by reference in their entirety to the same extent as if each such individual patent, publication and database entry were specifically and individually indicated to be incorporated by reference and were set forth in its entirety herein.

EXAMPLES

1. Materials

Where the source of a reagent is not specifically given herein, such reagent may be obtained from any supplier of reagents for molecular biology at a quality/purity standard for application in molecular biology.

Synthesis of 1-O-{4-[(2-cyanoethoxy)-N,N-diisopropylamino-phosphanyloxy]-butyl}-6-O-(4-methoxytriphenylmethyl)-2,3,4-tri—O-acetyl-B-D-galactopyranoside (9)

Figure 6:
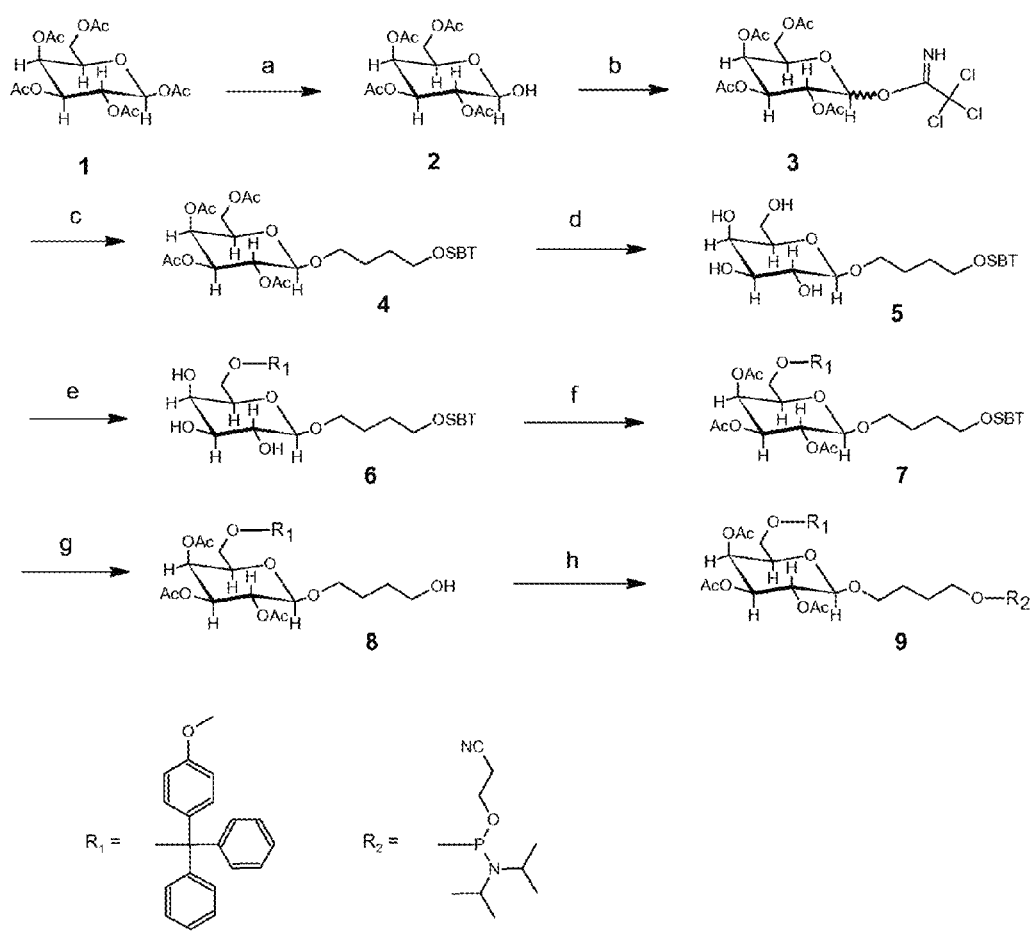
FIG. 6 depicts the synthesis scheme for 1-O-{4-[(2-cyanoethoxy)-N,N-diisopropylamino-phosphanyloxy]-butyl}-6-O-(4-methoxytriphenylmethyl)-2,3,4-tri-O-acetyl-β-D-galactopyranoside. Reagents and conditions: (a) Benzylamine, THF; (b) DBU, $CCl_3CN$, $CH_2Cl_2$ (71.5%); (c) 4-(tert-butyldimethylsilyloxy)-1-butanol, AgOTf, $CH_2Cl_2$, −78° C. (77.9%); (d) Sodiummethylate, MeOH; (e) MMT-Cl, Pyridine; (f) Acetanhydride, Pyridine (39.6%); (g) tert-butyl-ammoniumfluoride, THF (70.2%); (h) 2-cyanoethyl-N,N,N,N-tetraisopropylphosphane, DIPEA, ETT, ACN (74.3%).

The synthesis of compound 9 is illustrated in FIG. 6. 20 g (51.24 mmol) of β-D-galactosepentaacetate 1 was dissolved in 150 ml THF and 6.7 ml (61.49 mmol) of benzylamine was added with a dropping funnel. The reaction was stirred for 18 h at room temperature to give 2,3,4,6-tetra-O-acetyl-β-D-galactopyranose 2.

Product 2 was dissolved in 50 ml (240 mmol) trichloroacetonitrile and cooled down to −20° C. Within 15 min 3.56 ml (23.96 mmol) of 1,8-Diazabicyclo[5.4.0]-undec-7-ene were added using a dropping funnel. After 1.5 h synthesis of 2,3,4,6-tetra-O-acetyl-D-galactopyranosyl-trichloroacetimidate 3 was completed and the solvent was removed under reduced pressure. The residue was chromatographed over Kieselgel60 using cyclohexane/acetic acid ethyl ester 4:1 and product 3 was obtained in 71.5% yield.

19 g (38.38 mmol) of product 3 were dissolved in 150 ml $CH_2Cl_2$ and 13.34 ml (57.57 mmol) 4-(tert-butyldimethylsilyl)-oxy-1-butanole was added. 2.47 g (9.59 mmol) Silver-trifluoromethansulfonate in 0.5 ml Toluol was dissolved in a flask and cooled down to −78° C. Product 3 was added over a dropping funnel within 10 min and reaction was stirred for 20 h. Afterwards 0.3 eq. triethylamine were added and the mixture was diluted with 50 ml $CH_2Cl_2$ for extraction with 0.2 M HCl and sodium hydrogen carbonate. The solution was dried over $Na_2SO_4$ and solvent was removed under reduced pressure. 1-O-(4-tert-butyl-dimethylsilyloxybutyl)-2,3,4,6-tetra-O-acetyl-β-D-galactopyranoside 4 was purified over Kieselgel60 (cyclohexane/acetic acid ethyl ester 6:1) in 77.9% yield.

To obtain 1-O-(4-tert-butyl-dimethylsilyloxy)-β-D-galactopyranoside 5 product 4 (15.28 g 29.29 mmol) was dissolved in 30 ml methanol and 2 ml sodium methylate (25% in methanol) were added at room temperature. The mixture was stirred for 3 h and an equal amount of methanol was added as well as portions of an anionic exchange material Amberlit IR-120 to generate a pH around 7.0. The Amberlit was removed by filtration, the solution was dried with $Na_2SO_4$ and the solvent was removed under reduced pressure.

For protecting C6-OH by a monomethoxytrityl group (MMT) product 5 was dissolved in 30 ml pyridine and converted with 23.5 g (59 mmol) 4-Methoxytrityl-chloromethane into the corresponding 1-O-[4-tert-butyl-dimethylsilyloxybutyl]-6-O-(4-methoxytriphenylmethyl)-β-D-galactopyranoside 6 (MacKellar et al., Nucleic Acids Res 1992, 20:3411).

Product 6 (theoretically 29.29 mmol) was then peracetylated without any purification using 33 ml (351,5 mmol) acetic anhydride (99%) in additionally 15 ml pyridine. After 16 h the synthesis of von 1-O—[4-tert-butyl-dimethylsilyloxybutyl]-6-O-(4-methoxytriphenylmethyl)—2,3,4-tri-O-acetyl-β-D-galactopyranoside 7 was completed and solvent was removed under reduced pressure. The residue was chromatographed over Kieselgel60 using cyclohexane/acetic acid ethyl ester 10:1 in order to give product 7 in 39.6% yield.

Product 7 was dissolved in 15 ml THF and 4 ml (22.25 mmol) of tetrabutylammoniumfluoride (1 M in THF) were added using a dropping funnel (1 drop/sec). 24 h later the separation of the protecting group was completed 1-O—[4-hydroxybutyl]-6-O-(4-methoxytriphenylmethyl)—2,3,4-tri-O-acetyl-β-D-galacto-pyranoside 8 was obtained in 70.2% yield.

$^1$H-NMR (300 MHz), CDCl$_3$): 4.90-5.00 (d, J1/2=6.77 Hz, 1H, H-1β).

$^{13}$C-NMR (75 MHz), CDCl$_3$): δ=171.1-169.9 (3C, O=C—CH$_3$); 158.6 (p-Ar); 144.8 (2C, C$^{MMT}$-3); 136.0 (C$^{MMT}$-2); 130.9 (2C, o'-Ar); 128.3 (4C, m'-Ar); 127.7 (4C, m'-Ar); 126.9 (4C, p'-Ar); 113.1 (2C, m-Ar); 103.1 (C-1β); 86.4 (C$^{MMT}$-1); 72.8 (C-2); 72.5 (C-3); 72.0 (C-4); 70.3 (C-5); 69.3 (C-1'); 68.0 (C-4'); 62.3 (C-6); 55.1 (O—CH$_3$); 26.8 (C-2'); 26.4 (C-3'); 22.6 (3C, O=C—CH$_3$).

In order to synthesize OF1—O-{4-[(2-cyanoethoxy)-N,N-diisopropylamino-phosphanyloxy]-butyl}-6-O-(4-methoxytriphenylmethyl)-2,3,4-tri-O-acetyl-β-D-galactopyranoside 9 product 8 (3.5 g; 5.38 mmol) was dissolved in 20 ml acetonitrile and filled in a flask that previous was equilibrated with argon using a needle. Subsequently 1,12 ml (6.45 mmol) N-ethyldiisopropylamine, 2.65 ml (8.07 mmol) 2-cyanoethyl-N,N,N,N-tetraisopropylphosphane and 11.8 ml (5.92 mmol) S-ethylthiotetrazole (0.5 M) were added using a needle. After 1.5 h conversion into the phosphoramidite was completed and the mixture was extracted with a sodium chloride solution and dried over $Na_2SO_4$. The solvent was removed under reduced pressure and the residue was chromatographed (cyclohexane/acetic acid ethyl ester 3:1) to give product 9 in 74.3% yield as a white crystalline solid.

Synthesis of siRNAs

Single-stranded RNAs were produced by solid phase synthesis on a scale of 1 μmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Figure 7:
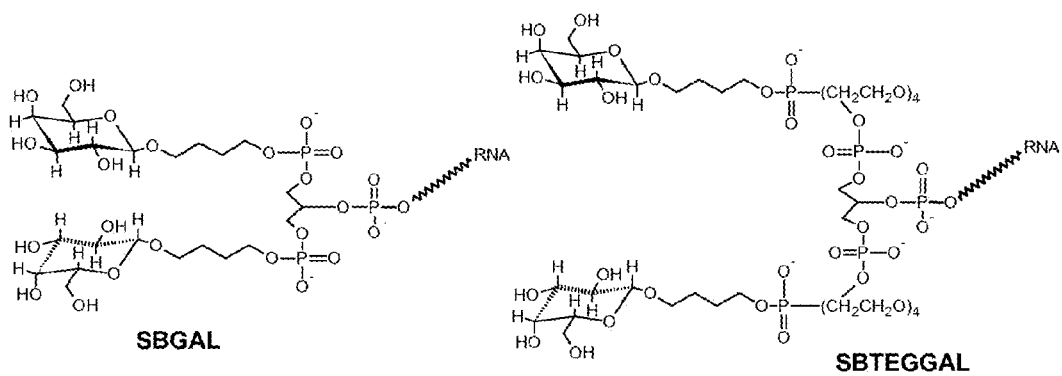
FIG. 7 depicts the chemical structures of SBGAL and SBTEGGAL siRNA conjugates. The SBGAL conjugate was generated by coupling a symmetrical branching linkage (SB) during RNA solid phase synthesis to the 5'-end of the sense strand followed by coupling of the galactose phosphoramidite 9. The SBTEGGAL conjugate additionally contained a tetraethylene glycol linkage (TEG) between the SB linkage and the sugar moiety.

Galactose conjugated siRNAs were synthesized using the same protocols as above with additional coupling of a symmetrical branching CED phosphoramidite (SB, ChemGenes) and the synthesized galactose amidite 9 (FIG. 7). In case of the SBTEGGAL modification a tetraethylene glycol (TEG, ChemGenes) was introduced between the SB linkage and the galactose moiety.

RNA synthesis of the Chol-siRNAs started from a controlled pore glass solid support carrying a cholesterol-aminocaproic acid-pyrrolidine linker, the synthesis of which is described elsewhere (Soutschek et al., Nature 2004, 432:173; US patent application, publication number 20060105976). To generate fluorescently labeled antisense strands an additional coupling of an Indodicarbocyanine-3-1-o-CED-phosphoreamidite (Cy3, ChemGenes) at the 5' end of the antisense strand was performed.

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany), and products characterized by ES mass spectrometry. Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was diluted to a concentration of 50 µmole double stranded RNA/I and stored at −20° C. until use.

The siRNAs used in this study consisted of a 21-nucleotide sense strand and a 23-nucleotide antisense strand resulting in a two-nucleotide overhang at the 3' end of the antisense strand. ApoB siRNA (ORF position 10049-10071): sense 5'-GUCAUCACACUGAAUACCAA*U-3' (SEQ ID NO: 1); antisense 5'-AUUGGUAUUAGUGUGUGAc* a*C-3' (SEQ ID NO: 2); bc12 siRNA: sense 5'-GGCCUUCUUUGAG-UUCGGUGG-3' (SEQ ID NO: 3); antisense 5'-CCAC-CGAACUCAAAGAAGGCcaC-3' (SEQ ID NO: 4); gfp siRNA: sense 5'-CCACAUGAAGCA GCACGACUU-3' (SEQ ID NO: 5); antisense 5'-AAGUCGUGCUGCUUCAU-GUG guC-3' (SEQ ID NO: 6). The lower-case letter represent 2'-O-methyl-modified nucleotides; asterisks represent phosphorothioate linkages.

To generate siRNAs from RNA single strands, equimolar amounts of complementary sense and antisense strands were mixed and annealed and siRNAs were further characterized by gel electrophoresis.

In Vitro Activity and Silencing Experiments

To determine the in vitro activity of siRNAs, HuH7 cells were transfected with siRNAs using oligofectamine (Invitrogen) and siRNA concentrations ranging from 0.1 nM to 100 nM. ApoB protein content was determined from cell culture supernatant by a sandwich ELISA capturing apoB with a polyclonal goat anti human apoB antibody (Chemicon International). ApoB detection was performed 48 h after transfection with a horseraddish peroxidase-conjugated goat anti human apoB-100 polyclonal antibody (Academy Bio-Medical Company). The remaining apoB content was calculated as the ratio of apoB protein in the supernatant of the cells treated with apoB-specific siRNA to the apoB protein in the supernatant of cells treated with unrelated control siRNAs. The QuantiGene assay (Genospectra) was used to quantify the reduction of apoB mRNA after siRNA treatment. Lysates from the cells were directly used for apoB and gapdh quantification, and the ratio of apoB and gapdh mRNA was calculated and expressed as a group average relative to cells treated with unrelated control siRNAs. Specific probes for detection of apoB and gapdh mRNA levels were designed to the following regions of the mRNA ORF: probe set apoB 8374-8776; probe set gapdh 252-472.

The complete panel of siRNAs was also evaluated for the ability to mediate posttranscriptional silencing of the apoB gene expression without using a transfection reagent. For these experiments cells were incubated with the same siRNAs used in the transfection experiments in concentrations at 10 µM, 5 µM and 1 µM siRNA. Cells were seeded in serum free media and the siRNAs were added. Four hours after siRNA donation fetal calf serum was added and 48 h after siRNA administration protein and mRNA contents were determined as described above. The same experiments was performed with HuH7 cells cultured in 5 mM $CaCl_2$ to activate the asialoglycoprotein receptor. After washing and seeding of the cells the siRNAs were added in the same concentrations as mentioned above.

For competition experiments HuH7 cells were incubated with 1 mM N-acetylgalactosamine at 37° C. in serum free media and siRNAs were added after 30 min in concentration at 10 µM, 5 µM and 1 µM. 48 h after siRNA administration protein and mRNA contents were determined as outlined above.

Fluorescence Microscopy and Uptake Studies

To determine an uptake of the galactose conjugated siRNAs into the cytoplasm the sense strands were annealed with a Cy3 (Indodicarbocyanine 3) labeled antisense strand. After an incubation time of 16 h and a siRNAs concentration of 10 µM the cell culture media was removed and cells were washed twice with PBS to eliminate siRNAs that were not taken up by the cells and 100 µl/well of normal media was added. Accordingly 10 µl/well of a 0.1 mg/ml stock solution of 4',6-Diamidino-2-phenylindoldihydrochloride (Sigma) were added and the cells were incubated for 30 min at 37° C. After washing the cells twice with PBS and adding fresh media the fluorenscence exposures were performed with an Olympus IX50 microscope and a monochrome camera (7.0 monochrome IR, Diagnostic Instruments) and pictures were analyzed with the MetaView Imaging software (Visitron Systems). To visualize the Cy3 fluorescence a NIB ($Ex_{max}$ 547/$Em_{max}$ 563 nm) filter was used and the exposure of the DAPI fluorescence was performed with a NB filter ($Ex_{max}$ 365 nm). Completing an overlay of both fluorescence exposures were created using the MetaView Imaging software.

In this study we describe the synthesis of galactose conjugated siRNAs. Using this approach it was undertaken to generate uptake via receptor mediated processes in liver cells as shown from Biessen and colleagues with galactose modified molecules (Biessen et al., Biochem. J. 1999, 340(Pt 3):783; Biessen et al., Methods Enzymol. 2000, 314:324; Rensen et al., J. Biol. Chem. 2001, 276:37577). Glycoconjugation of siRNAs with branched structures comprising galactose was selected to target the asialoglycoprotein receptor. A phosphoramidite was generated from β-D-Galactosepentaacetate as outlined in FIG. 6 and two different 5'-modified siRNAs were synthesized on solid phase.

Two linkage structures broadened the chemical space probed by this investigation. First a symmetrical branching linker (SB) was coupled to the 5'-end of the sense strand during solid phase synthesis followed by coupling of the galactose phosphoramidite 9 to generate the SBGAL conjugate (FIG. 7). The second approach used an additionally inserted tetraethylene glycol linkage (TEG) between the symmetrical branching linker and the galactose residues to synthesize the SBTEGGAL conjugate. This procedure aimed for an increased distance (~16 Å) between the negatively charged siRNA and the sugar moiety, because it was already shown that an upper gap advance the binding and internalisation via the asialoglycoprotein receptor (Biessen et al., Biochem. J. 1994, 302(Pt 1):283).

In Vitro Studies with Modified siRNAs Using a Transfection Agent

The ability of the above described conjugates to mediate posttranscriptional silencing of the apoB gene expression was demonstrated by classic transfection experiments using oligofectamine (FIG. 1). Silencing of the apoB mRNA would be expected to result in a corresponding reduction in apoB 100 protein levels. The apoB 100 protein and mRNA levels were measured by enzyme-linked immunosorbent assay (ELISA) and b-DNA in HuH7 hepatocarcinoma cells after transfection at siRNA concentrations ranging from 100 nM to 0.1 nM. The data are presented as mean values with corresponding standard diviation of three assays in triplicates normalized to the average level of unrelated siRNAs (b442, b442SBGAL and gfp3'Chol). Both galactose conjugated siRNAs SBGAL and SBTEGGAL are able to reduce the apoB 100 protein and mRNA content in a dose dependant manner comparable to that of the unmodified apoB sequence. As shown in FIGS. 1a and b, cells treated with 100 nM SBGAL and SBTEGGAL modified siRNAs showed statistically significant reductions (mean±s.d.; protein: SBGAL 87±5%; SBTEGGAL 73±3% and mRNA: SBGAL 79±9%; SBTEGGAL 71±7%) in apoB 100 protein and mRNA levels as compared with the mean of the unspecific controls (P*<0.001). The 3'Chol modified siRNA used as a positive control in all experiments (Soutschek et al., Nature 2004, 432:173) showed a lower silencing effect at the same siRNA concentration compared to that of the suger conjugated and unmodified siRNAs (mean±s.d.; protein: 52%±14%; mRNA: 69±8%). In summary, the 5'-modification of the sense strand with branched galactose structures did not affect the in vitro activity of these compounds to mediate a posttranscriptional silencing of the apoB gene expression.

Delivery Experiments in the Absence of a Transfection Agent

Figure 2:
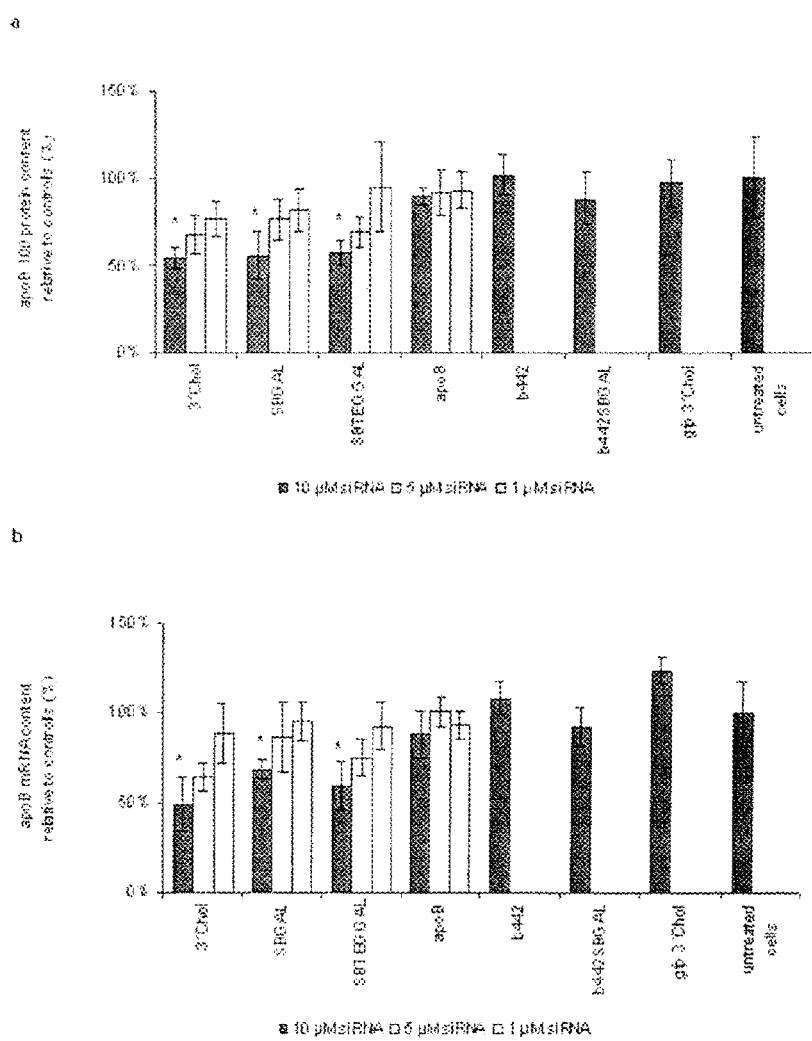
FIG. 2 depicts the results of siRNA delivery experiments (10 μM, 5 μM, 1 μM siRNA) in the absence of transfection agents in HuH7 cells. Apo B 100 protein and mRNA contents were determined relative to the mean value of unspecific siRNAs (n=9). Statistical analysis was done by t-test, P*<0.005 compared to unspecific controls.

Glycoconjugation of the siRNA with branched galactose structures was selected to target the asialoglycoprotein receptor (ASGPR). To demonstrate the ability of galactose conjugated siRNAs SBGAL and SBTEGGAL to silence apoB expression in vitro without using transfection agents HuH7 cells were incubated with these siRNAs in concentrations ranging from 10 µM to 1 µM and protein and mRNA levels were determined using ELISA and b-DNA (FIGS. 2a and b). The results presented in FIGS. 2a and b show that incubation with galactose modified siRNAs resulted in a dose-dependent significant decrease of apoB 100 protein and mRNA content (P*<0.005). Using a dose of 10 µM SBGAL conjugated siRNA the apoB 100 protein was reduced to 56±14% and the mRNA content decreased to 68±5%. The SBTEGGAL conjugate also caused a reduction of the protein level (mean±s.d.; 58±7%) and mRNA content (60±14%) compared to unrelated siRNAs. Furthermore the 3'Chol modified siRNA permitted a decrease of apoB protein and mRNA equal to that of the suger conjugated siRNAs at a concentration of 10 µM siRNA (mean±s.d.; protein: 54±6%; mRNA: 49±15%). In contrast cells treated with the unmodified apoB siRNA showed no significant reduction in the apoB 100 protein or mRNA levels, because as expected due to their negative charge and high molecular weight unmodified siRNAs are not able to cross cellular membranes. Ultimately, a dose-dependent reduction of apoB protein and mRNA contents could be demonstrated in the absence of any transfection reagent using galactose modified siRNAs, suggesting receptor mediated uptake.

Figure 3:
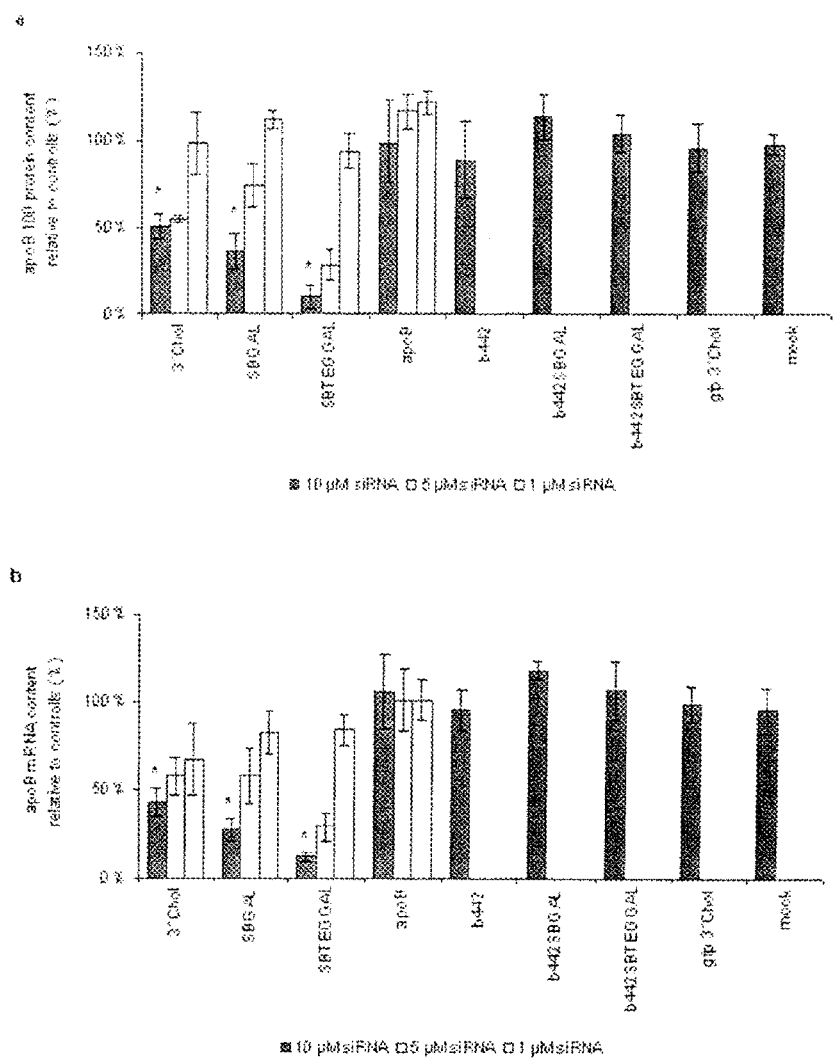
FIG. 3 depicts the in vitro silencing of apoB 100 protein and mRNA in HuH7 cells after receptor activation with 5 mM $CaCl_2$ and siRNA treatment (10 μM, 5 μM and 1 μM siRNA) in the absence of transfection agents. Apo B 100 protein and mRNA contents were determined relative to the mean value of unspecific siRNAs (n=9). Error bars illustrate standard deviation (s.d.) of the mean values. Statistical analysis was done by t-test, P*<0.0001 compared to unspecific controls.

Improved Silencing Effects for Galactose Conjugated siRNAs Upon Receptor Activation The galactose conjugated siRNAs were synthesized to target the asialoglycoprotein receptor (ASGPR), which is expressed on the cell surface of hepatocytes. The ASGPR is capable of internalizing galactose terminated molecules (Biessen et al., Methods Enzymol 2000, 314:324; Biessen et al., Biochem J 1999, 340(Pt 3):783; Biessen et al., Biochem J 1994, 302(Pt 1):283; Rensen et al., J Biol Chem 2001, 276: 37577; Hangeland et al., Bioconj Chem 1995, 6:695; Duff et al., Methods Enzymol 2000, 313:297). These receptors belong to the family of C-type lectins, and their functionality is calcium dependent (Van Lenten and Ashwell, J Biol Chem 1972, 247:4633; Drickamer, J. Biol. Chem. 1988, 263:9557). To further confirm the mediation of uptake via the receptor, HUH7 cells were cultured in a growth medium containing 5 mM $CaCl_2$ in order to activate the receptor. In contrast the direct incubation experiments with the siRNAs were performed after removing the growth medium and washing the cells with PBS. The same procedure as for the incubation experiments without receptor activation was performed at siRNA concentrations ranging from 10 µM to 1 µM. Protein and mRNA levels were determined using ELISA and the b-DNA assay, and data evaluated as means with standard deviation relative to unrelated siRNAs (b442, b442SBGAL, b442SBTEGGAL and gfp3'Chol). As shown in FIGS. 3a and b, receptor activation with calcium chloride resulted in significantly improved and dose-dependent silencing effects by the galactose conjugated siRNAs, whereas the activity of the 3'Chol modified siRNA remained unaffected (P*<0.001). The SBGAL conjugated siRNA decreased apoB mRNA content by about 70±7% at a concentration of 10 µM siRNA. At the same concentration the siRNA containing an additional TEG linkage (SBTEGGAL) reduced mRNA content by 90±2%. Silencing of the mRNA resulted in corresponding decreases in protein levels (36±10%; 10±6%). Culturing the cells in calcium chloride had no effect on gene silencing by the unmodified apoB siRNA; as expected, no silencing was observed. Furthermore the unrelated siRNAs having the same galactose modifications as the apoB siRNAs also were not able to decrease apoB protein and mRNA contents. Thus, an unspecific effect of the galactose modification itself is excluded. The results presented herein additionally support a receptor mediated uptake for the galactose conjugated siRNAs SBGAL and SBTEGGAL.

Galactose Conjugated siRNAs are Localized in the Cytoplasm

Figure 5:
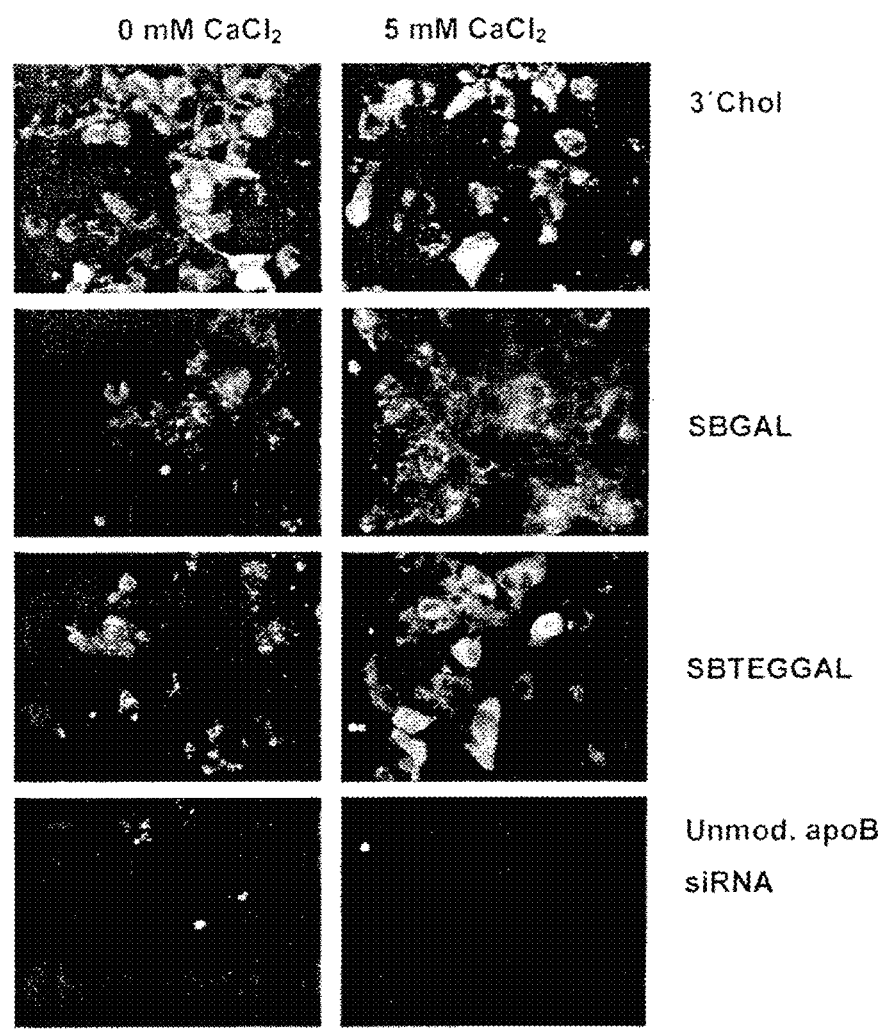
FIG. 5 depicts the results of delivery experiments with fluorescently labeled siRNAs (10 μM) in HuH7 cells after receptor activation with 5 mM CaCl2 (right panel) or without receptor activation (left panel) in the absence of transfection agents. Localisation of Cy3 labeled siRNAs was determined by fluorescence microscopy.

Due to the ability of the galactose modified siRNAs to silence the apoB gene expression it can be assumed that these siRNAs are able to cross the cellular membrane and enter the cytoplasm of the target cells without using a transfection agent. To determine the uptake into the cell fluorescently labeled siRNAs were used to visualize these siRNAs in intracellular compartments. Therefore cells were grown in the absence or presence of 5 mM calcium chloride to activate the asialoglycoprotein receptor and fluorescently labeled siRNAs were added at a concentration of 10 µM. 16 h after siRNA administration exposures were generated using fluorescence microscopy (FIG. 5). Internalisation of the modified apoB siRNAs was determined by 4',6-Diamidino-2-phenylindoldihydrochloride staining of the nucleus and fluorescence was localized around the nucleus (not shown). Cells grown in normal cell culture media and incubated with galactose modified siRNAs showed a minimal fluorescence within the cytoplasm (FIG. 5, left panel), whereas culturing the cells in 5 mM calcium chloride in order to activate the asialoglycoprotein receptor significantly enhance intracellular fluorescence (FIG. 5, right panel). In contrast the 3'-Cholesterol modified siRNA remained unaffected and these cells showed an equal distribution of the siRNA within the cytoplasm with or without receptor activation. Uptake of the unmodified apoB siRNA as well remained unaffected and no fluorescence could be detected within the cells. As expected, culturing the cells in 5 mM calcium chloride had no effect on the uptake of the unmodified apoB sequence. Hence, it was further demonstrated that the galactose conjugated siRNAs are selectively taken up by parenchymal liver cells upon receptor activation with calcium chloride.

Competition of Galactose Conjugated siRNAs with Other Ligands of the ASGPR

Figure 4:
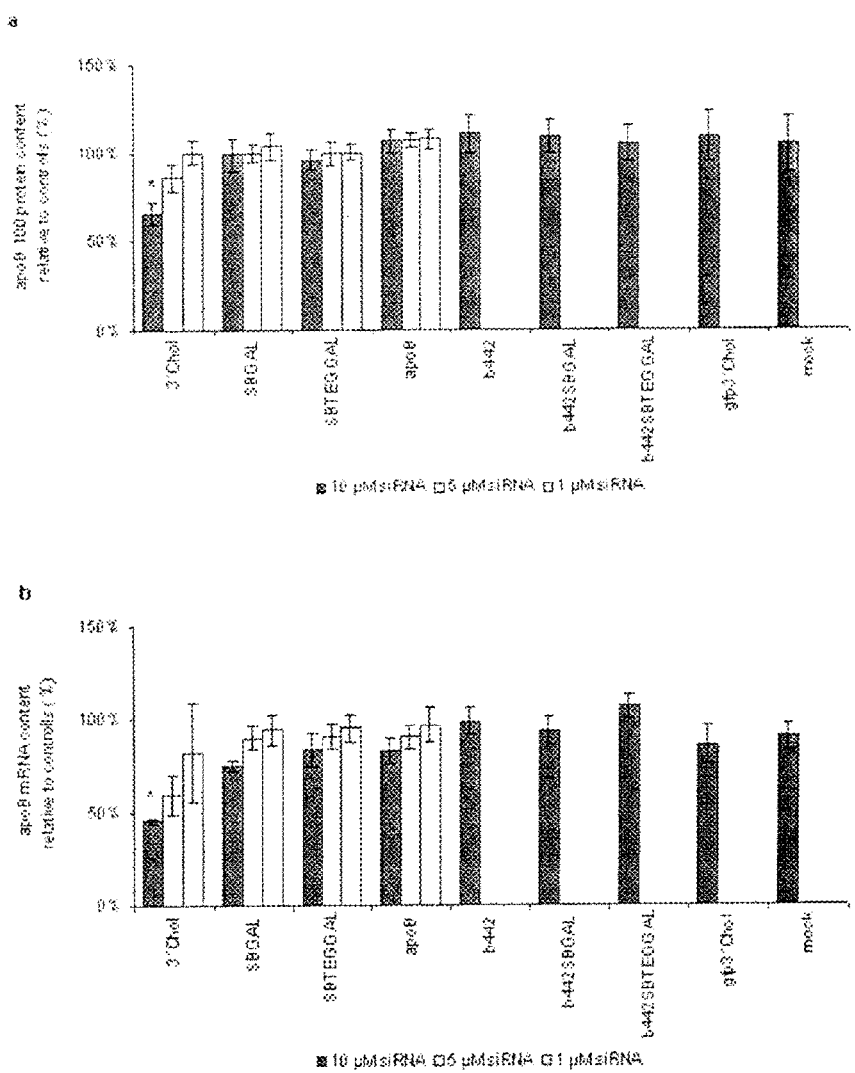
FIG. 4 depicts the results of competition experiments with 1 mM GalNAc on apoB 100 protein and mRNA levels after receptor stimulation and siRNA treatment (10 μM, 5 μM and 1 μM siRNA) in the absence of transfection agents in HuH7 cells. Apo B 100 protein and mRNA contents were determined relative to the mean value of unspecific siRNAs (n=6). Error bars illustrate standard deviations of the means. Statistical analysis was done by t-test, P*<0.0001 compared to unspecific controls.

To investigate whether the galactose conjugated siRNAs are specifically taken up by the asialoglycoprotein receptor, competition studies with N-acetylgalactosamine were performed. GalNAc is known to possess a 40 to 50-fold higher binding affinity for the ASGPR as compared to galactose (Rensen et al., J. Biol. Chem. 2001, 276:37577). Cells were seeded and preincubated for 30 min with 1 mM GalNAc and than the siRNAs were added in concentrations of 10 µM, 5 µM and 1 µM. As shown in FIG. 4 a and b, preincubation with GalNAc resulted in an almost complete inhibition of the silencing effect caused by the galactose conjugated siRNAs SBGAL and SBTEGGAL. No significant reductions in apoB protein and mRNA contents could be observed (protein content 10 µM SBGAL siRNA 99±9%; SBTEGGAL 96±6% and mRNA content SBGAL 75±3%; SBTEGGAL 84±10%). In contrast the RNA interference effect and resulting reduction in apoB protein and mRNA levels caused by the 3'-Cholesterol modified siRNA remained unaffected. These results further confirm that the galactose containing siRNAs are selectively taken up by the asialoglycoprotein receptor and that this uptake can be competed out by an excess of N-acetylgalactosamine, whereas the uptake of 3'-Chol conjugated siRNAs seems to occur via another mechanism.

We claim:

1. An RNAi agent for inhibiting the expression of a target gene in a cell, wherein the RNAi agent is a compound of formula (III):

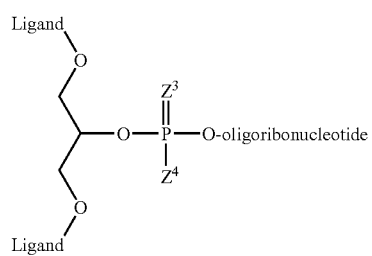

Formula (III)

wherein $Z^3$ and $Z^4$ are each independently O, S, OH, O$^-$, OR$^{11}$, Se, BH$_3^-$, H, NHR$^{12}$, N(R$^{12}$)$_2$, optionally substituted alkyl, optionally substituted cycloalkyl, optionally substituted aralkyl, optionally substituted aryl, or optionally substituted heteroaryl;

wherein R$^{11}$ and R$^{12}$ are each independently optionally substituted alkyl, optionally substituted cycloalkyl, optionally substituted aryl, optionally substituted aralkyl, optionally substituted heterocyclyl, optionally substituted heteroaryl or amino acid;

wherein the ligand comprises at least one galactose moiety and is coupled through at least one linker group

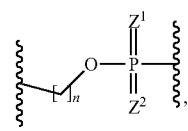

and at least one linker group —O—CH$_2$CH$_2$(OCH$_2$CH$_2$)$_n$OP(Z$^5$)(Z$^6$)—;

wherein $Z^1$, $Z^2$, $Z^5$ and $Z^6$ are each independently O, S, OH, O⁻, $OR^{11}$, Se, $BH_3^-$, H, $NHR^{12}$, $N(R^{12})_2$, optionally substituted alkyl, optionally substituted cycloalkyl, optionally substituted aralkyl, optionally substituted aryl, or optionally substituted heteroaryl;

wherein n is 1-20, and wherein at least one oligoribonucleotide strand is complementary to at least parts of an mRNA corresponding to the target gene.

2. The RNAi agent of claim 1 wherein the distance between the galactose moieties is at least 4 Å.

3. The RNAi agent of claim 2, wherein the distance between the galactose moieties is at least 10 Å.

4. The RNAi agent of claim 3, wherein the distance between the galactose moieties is at least 15 Å.

5. The RNAi agent of claim 4, wherein the distance between the galactose moieties is at least 20 Å.

6. The RNAi agent of claim 1 wherein the RNAi agent is capable of inhibiting the expression of the target gene in a cell.

7. The RNAi agent of claim 6, wherein the cell harbors the asialoglycoprotein receptor on its surface.

8. The RNAi agent of claim 6, wherein the cell is a hepatocyte.

9. A pharmaceutical composition comprising (i) at least one RNAi agent of the claim 1 and (ii) a pharmaceutical oligonucleotide strand.

10. A cell comprising an RNAi agent of claim 1.

11. The cell of claim 10, wherein the cell is a hepatocyte.

12. The RNAi agent of claim 1, wherein $Z^1$, $Z^2$, $Z^3$, $Z^4$, $Z^5$ and $Z^6$ are each independently O or S; and wherein each n independently ranges from 1-6.

13. The RNAi agent of claim 1, wherein $Z^1$, $Z^2$, $Z^3$, $Z^4$, $Z^5$ and $Z^6$ are each independently O.

14. The RNAi agent of claim 1, wherein each n is independently 2-4.

15. An RNAi agent for inhibiting the expression of a target gene in a cell, wherein the RNAi agent is represented as:

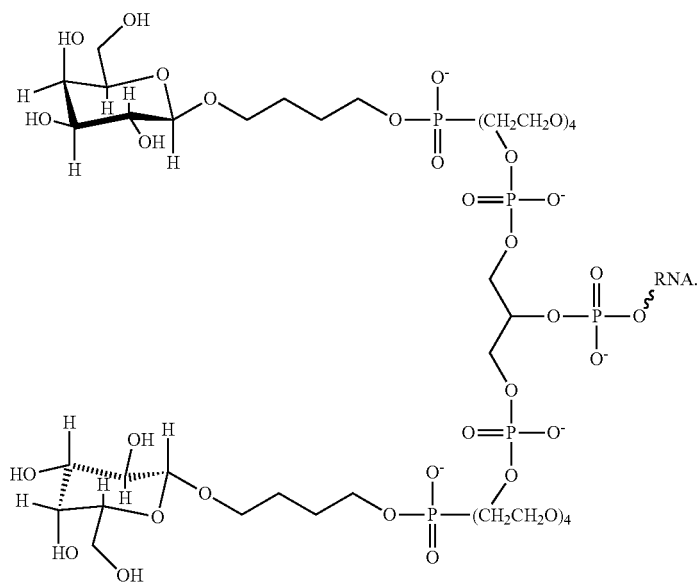

SBTEGGAL

* * * * *